(12) United States Patent
Methot

(10) Patent No.: US 9,411,910 B2
(45) Date of Patent: Aug. 9, 2016

(54) DENTAL ANALYSIS METHOD AND SYSTEM

(75) Inventor: Alain Methot, Lorraine (CA)

(73) Assignee: CENTRE DE RECHERCHE MEDICO DENTAIRE AM INC., Laval (CA)

(*) Notice: Subject to any disclaimer, the term of this patent is extended or adjusted under 35 U.S.C. 154(b) by 632 days.

(21) Appl. No.: 13/809,843

(22) PCT Filed: Jul. 13, 2011

(86) PCT No.: PCT/CA2011/000800
§ 371 (c)(1),
(2), (4) Date: Feb. 27, 2013

(87) PCT Pub. No.: WO2012/006717
PCT Pub. Date: Jan. 19, 2012

(65) Prior Publication Data
US 2013/0158958 A1   Jun. 20, 2013

Related U.S. Application Data

(60) Provisional application No. 61/344,392, filed on Jul. 12, 2010, provisional application No. 61/491,291, filed on May 30, 2011.

(51) Int. Cl.
*A61C 11/00*     (2006.01)
*G06F 17/50*    (2006.01)
*A61C 13/00*    (2006.01)
*G06F 19/00*    (2011.01)
(Continued)

(52) U.S. Cl.
CPC ............ *G06F 17/50* (2013.01); *A61C 13/0004* (2013.01); *G06F 19/321* (2013.01); *G06T 19/20* (2013.01); *A61B 1/005* (2013.01); *A61B 5/4547* (2013.01); *A61C 9/004* (2013.01); *A61C 11/00* (2013.01); *A61C 13/0013* (2013.01); *G06T 2219/2016* (2013.01)

(58) Field of Classification Search
None
See application file for complete search history.

(56) References Cited

U.S. PATENT DOCUMENTS 5,338,198 A * 8/1994 Wu .................... A61C 13/0004
                                                    433/213
6,261,248 B1 * 7/2001 Takaishi ................. A61B 5/103
                                                    378/39

(Continued)

FOREIGN PATENT DOCUMENTS

WO       2012/000511 A1      1/2012

*Primary Examiner* — Kibrom K Gebresilassie
(74) *Attorney, Agent, or Firm* — BCF LLP

(57) ABSTRACT

A system for designing the dentition of a patient, comprising a first input for providing an image of the smile of the patient to the system, an output, a processor for computing and applying a first set of visual indicators onto the image of the smile of the patient through the output, the first set of visual indicators indicating ideal positioning of the teeth of the patient, and for computing and applying a second set of visual indicators onto the image of the smile of the patient through the output, the second set of visual indicators providing adjustment of positioning of the teeth of the patient, a memory having stored therein a library of 2D digital images of smiles and associated 3D dentition models, a user interface for selecting a desired 2D digital image to be applied to the image of the smile of the patient and adjusting the second set of visual indicators, the adjustment of the second set of visual indicators modifying the 2D digital image, wherein the processor modifies the 3D dentition model associated with the 2D digital image and provides a virtual wax-up of a dental restoration of the dentition of the patient.

19 Claims, 31 Drawing Sheets

(51) Int. Cl.
*G06T 19/20* (2011.01)
*A61C 9/00* (2006.01)
*A61B 5/00* (2006.01)
*A61B 1/005* (2006.01)

(56) References Cited

U.S. PATENT DOCUMENTS

| | | |
|---|---|---|
| 7,153,135 B1 | 12/2006 | Thomas |
| 8,092,220 B2 | 1/2012 | Wiedmann |
| 8,376,745 B2 * | 2/2013 | Stonisch ............... 433/215 |
| 8,423,335 B2 | 4/2013 | Methot |
| 8,706,672 B2 * | 4/2014 | Malfliet et al. ........... 706/47 |
| 8,753,119 B2 * | 6/2014 | Fang ............... A61C 11/00 433/213 |
| 2003/0204150 A1 * | 10/2003 | Brunner ............ A61B 5/1114 600/590 |
| 2003/0224314 A1 * | 12/2003 | Bergersen .................. 433/6 |
| 2005/0070782 A1 * | 3/2005 | Brodkin ............ A61C 19/045 600/407 |
| 2005/0089822 A1 * | 4/2005 | Geng ..................... 433/215 |
| 2006/0003292 A1 * | 1/2006 | Lauren ............... A61C 5/007 433/215 |
| 2006/0127836 A1 * | 6/2006 | Wen ................... A61C 7/00 433/24 |
| 2007/0099147 A1 * | 5/2007 | Sachdeva ............. A61C 7/00 433/24 |
| 2009/0162813 A1 * | 6/2009 | Glor et al. .............. 433/196 |
| 2009/0291408 A1 * | 11/2009 | Stone-Collonge .. G06F 19/3437 433/24 |
| 2009/0306939 A1 * | 12/2009 | Methot ..................... 703/1 |
| 2010/0049351 A1 * | 2/2010 | Monkmeyer ....... A61C 13/0004 700/98 |
| 2010/0191510 A1 * | 7/2010 | Kopelman ......... A61C 13/0004 703/1 |
| 2010/0332253 A1 * | 12/2010 | Adusimilli ............ A61C 11/00 705/2 |
| 2011/0196524 A1 * | 8/2011 | Giasson et al. ........... 700/103 |
| 2011/0196653 A1 * | 8/2011 | Lajoie et al. ............... 703/1 |
| 2012/0095732 A1 * | 4/2012 | Fisker et al. ............... 703/1 |
| 2013/0017507 A1 * | 1/2013 | Moffson ................ A61C 1/084 433/27 |
| 2013/0158958 A1 * | 6/2013 | Methot ............... A61C 13/0004 703/1 |
| 2013/0216972 A1 * | 8/2013 | Kolozsvary .......... A61C 1/0046 433/29 |
| 2013/0218530 A1 * | 8/2013 | Deichmann ........ A61C 13/0004 703/1 |
| 2014/0313304 A1 * | 10/2014 | Adriaens ............... A61C 11/005 348/77 |

* cited by examiner

DENTAL ANALYSIS METHOD AND SYSTEM

CROSS-REFERENCE TO RELATED APPLICATION

This application claims the benefits of U.S. provisional patent applications No. 61/344,392 filed Jul. 12, 2010 and No. 61/491,291 filed May 30, 2011; which are hereby incorporated by reference.

TECHNICAL FIELD

The present disclosure relates to a dental analysis method and system. More specifically, the present disclosure relates to an analysis method and system for the evaluation, planning and modification of the dentition of a patient.

BACKGROUND

In the study of what is considered "beautiful", in nature, human features, architecture, art, etc., it was discovered that there is a common principle at work. This common principle is the universal recognition of pleasant proportions. People have an inherent ability to recognize that an art object has good or bad proportions, or that a person's torso compared to his/her legs looks too long, or too short and out of proportion. This universal common principle thread of proportion, known since antiquity, is referred to the Golden Proportion or Divine Proportion.

Human beauty is also governed by the Golden Proportion. Squares based on the Golden Proportion have been used to define the ideal location of the pupils and outside corners of the mouth. Lines based on the Golden Proportion have been used to define, for example, the ideal positioning of the nose, the tip of the nose, the inside of the nostrils, the two rises of the upper lip, the inner points of the ear, the distance from the upper lip to the bottom of the chin, as well as the width of the nose, the distance between the eyes and eye brows and the distance from the pupils to the tip of the nose.

The Golden Proportion has also been used to study the human dentition. The four front teeth, from central incisor to premolar constitute the most significant part of the dentition and they are in the proportion to each other although they don't exactly follow the Golden Proportion. Regardless, the Golden Proportion has been combined in a grid which may be used to assist in perfecting the aesthetics of the front teeth. However, such grid displays the four front teeth with mitigated results. Only the upper centrals and sometimes the upper laterals follow the Golden Proportion, the other Maxillary teeth usually do not. Accordingly, there is a need for an analysis method and system for the evaluation, planning and modification of the dentition of a patient In the present specification, there are described embodiments of a method and system designed to overcome the above-described limitations of the conventional techniques.

SUMMARY

The present disclosure relates to a system for designing the dentition of a patient, comprising:
- an first input for providing an image of the smile of the patient to the system;
- an output;
- a processor for computing and applying a first set of visual indicators onto the image of the smile of the patient through the output, the first set of visual indicators indicating Ideal positioning of the teeth of the patient, and for computing and applying a second set of visual indicators onto the image of the smile of the patient through the output, the second set of visual indicators providing adjustment of positioning of the teeth of the patient;
- a memory having stored therein a library of 2D digital images of smiles and associated 3D dentition models;
- a user interface for selecting a desired 2D digital image to be applied to the image of the smile of the patient and adjusting the second set of visual indicators, the adjustment of the second set of visual indicators modifying the 2D digital image;
- wherein the processor modifies the 3D dentition model associated with the 2D digital image and provides a virtual wax-up of a dental restoration of the dentition of the patient.

The present disclosure further relates to a method of performing the as described above.

BRIEF DESCRIPTION OF THE DRAWINGS

A non-limitative illustrative embodiment of the disclosure will now be described by way of example only with reference to the accompanying drawings, in which:

FIG. 2 is a front view illustration of the upper teeth of an

FIG. 36 is an elevation view of the platform on an articulator with an adjustable M Proportion ruler template on which is positioned a maxillary model or cast according to given measurements;

DETAILED DESCRIPTION

Generally stated, the non-limitative illustrative embodiment of the present disclosure provides a method and system for the evaluation, planning and modification of the dentition of an individual, such as, for example, a patient, by the application of generally vertical lines, hereby referred to as "positioning lines" (Y axis), following the herein disclosed M Proportion, which may be determined either explicitly or implicitly from measurements such as, for example, central incisor width and inter-molar distance, onto the dentition of the patient in order to determine "ideal" positioning of the patient's teeth, and by the application of an horizontal line (X axis) apposed on the incisal edges of the upper centrals. In one embodiment, the resulting positioning lines may be applied to 2D or 3D digital images, X-rays, computed tomography (CT) scans, etc., of the patient's dentition or may be included as part of a modeling or re-modeling software to dispose the teeth when creating, for example, ceramic teeth, orthodontic molds, dentures, etc. in a further embodiment, the positioning lines may be angled at a specific angle in order to address an occlusion condition or for aesthetical considerations.

Golden Proportion

Figure 1:
FIG. 1 is a schematic diagram illustrating the Golden Proportion concept.

The Golden Proportion, or Divine Proportion, represents a ratio of 1:1.618. It has been used in a multitude of applications and is well known in the art Briefly speaking, referring to FIG. 1 the Golden Proportion may be expressed as:

$$\frac{AB}{CB} = \frac{CB}{AC} \quad \text{Equation 1}$$
$$= 1.618.$$

For example, if the distance AB is 10 mm, then the distance AC will be 3.82 mm and CB will be 6.18 mm.

Dentition

Figure 2:
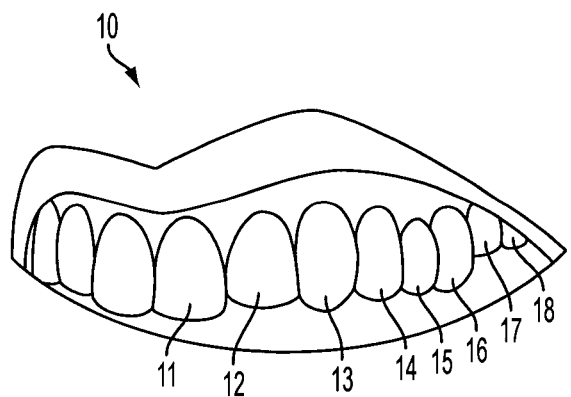

Referring to FIG. 2, the dentition (10) generally comprises the central incisor (11), the lateral incisor (12), the canine (13), the first premolar (14), the second premolar (15) and the first molar (16). The second (17) and third (18) molars are usually not visible in the smile. It is to be understood that for the purpose of clarity FIG. 2 only shows the left side of the dentition (10), the right side being symmetrical.

For the sake of clarity, from thereon reference will be made to the positioning lines on either the left side or the right side of the dentition (10) but it is to be understood that by virtue of symmetry, the same comments apply to the positioning lines on other side of the dentition (10).

Application of the Golden Proportion

Figure 3:
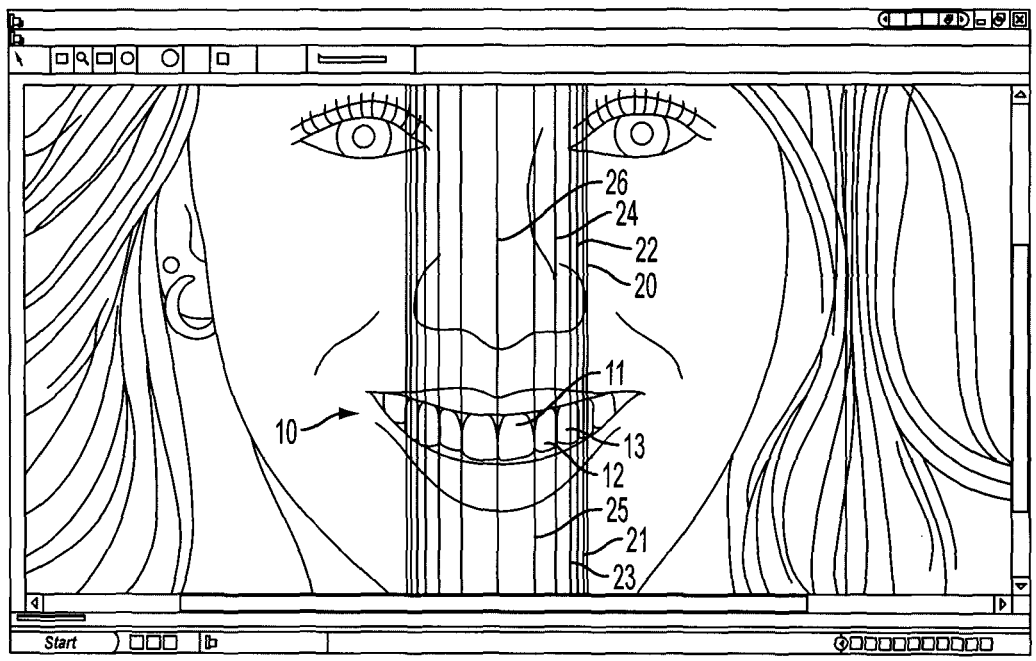
FIG. 3 is a front view image of the smile of an individual on which are superimposed positioning lines following a Golden Proportion with a ratio of 1:1.618.

Referring to FIG. 3, there is shown a front view image of a patient's dentition (10) on which is applied the Golden Proportion (ratio of 1:1.618) with seven positioning lines, resulting in a center positioning line (26) and six side positioning lines (25, 24, 23, 22, 21, 20) on one side of the dentition (10). The center positioning line (26) is positioned at the center of the dentition (10) and the last side positioning line (20) is positioned by the user such that the second positioning line (25) is positioned between the central incisor (11) and the lateral incisor (12). Once the first (26) and last positioning lines (20) are positioned, the remaining side positioning lines (25, 24, 23, 22, 21) are computed using the Golden Proportion with a ratio of 1:1.618.. As may be seen in FIG. 3, the position of the central incisor (11) and the lateral incisor (12) generally correspond to side positioning lines (25) and (24), respectively, but the position of the canine (13) does not fit with side positioning line (23), the side positioning line (23) actually passing in the middle of the canine (13).

Application of the M Proportion

Figure 4:
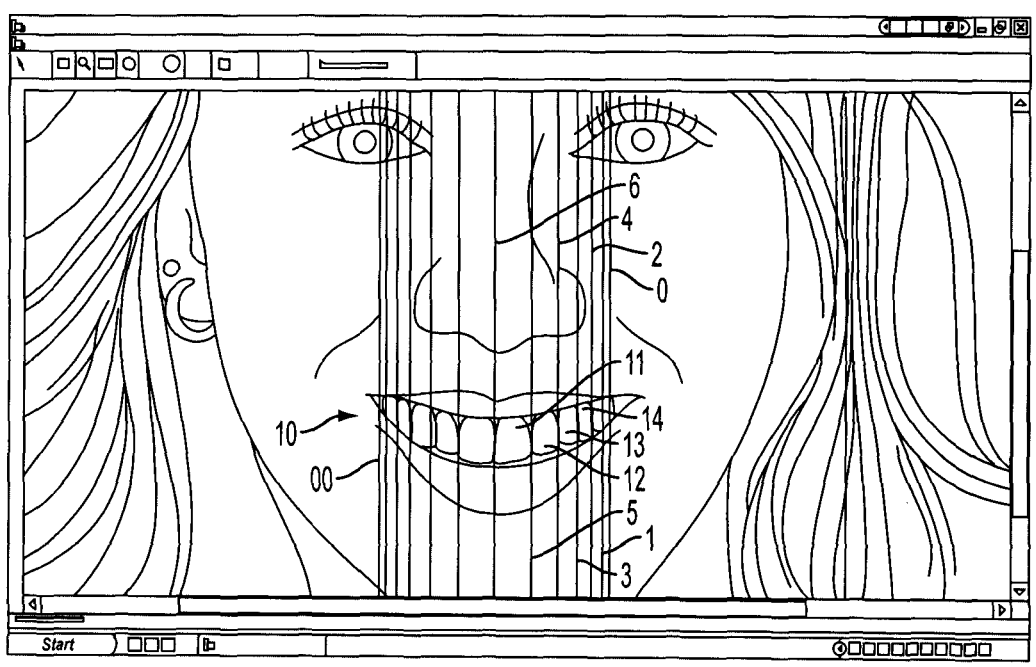
FIG. 4 is a front view image of the smile of an individual on which are superimposed positioning lines following the M Proportion with a ratio of 1:1.367.

Referring now to FIG. 4, there is shown an image of the patient's smile on which is applied the M Proportion (ratio of 1:1.367) with seven positioning lines, resulting in a center positioning line (6) and six side positioning lines (5, 4, 3, 2, 1, 0) on one side of the dentition (10). The center positioning line (6) is fixed at the center of the dentition (10) and the last side positioning line (0) is positioned by the user, advantageously on the buccal face of the first molar (16), the remaining side positioning lines (5, 4, 3, 2, 1) being computed using the M Proportion with a ratio of 1:1.367. As may be seen in FIG. 4, the position of the central incisor (11), the lateral incisor (12), the canine (13) and the first premolar (14) generally correspond to side positioning lines (5), (4), (3) and (2), respectively. In an idealized view, shown in FIG. 9, it may be seen that the M Proportion may be used to position the central incisor (11), the lateral incisor (12), the canine (13), the first premolar (14), the second premolar (15) and the first molar (16) on a virtual wax-up of a patient using side positioning lines (5), (4), (3), (2), (1) and (0), respectively. Furthermore, referring to FIG. 12, the M Proportion may be used with a real wax-up of the patient, which in turn is used to create, for example, crowns for the patient. Thus, in this illustrative embodiment, using the M Proportion, 12 front teeth (six on each side) of the dentition (10) were positioned instead of only four, as seen in FIG. 3. It is to be understood that the same technique described above using seven positioning lines for the positioning of 12 front teeth may also be extended to, for example, nine positioning lines permitting the positioning of 16 teeth. The number of teeth visible in the smile may vary from patient to patient depending on the physiognomy of the patient.

Figure 19:
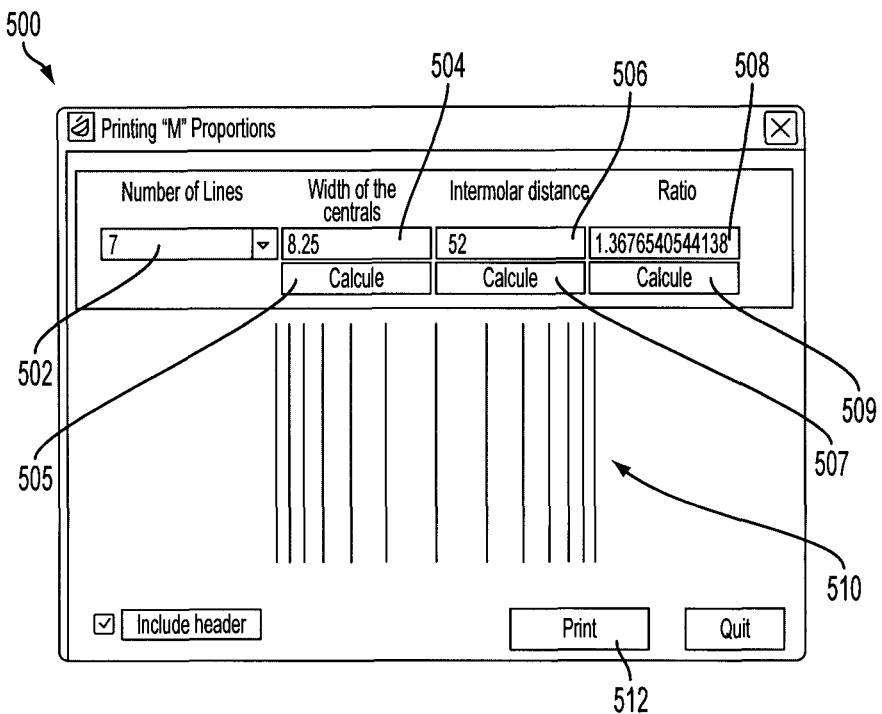
FIG. 19 is an example of the M Proportion calculator interface.

Although in M Proportion with a ratio of 1:1.367. was used in FIG. 4, it is to be understood that it may vary depending on the physiognomy of the patient or the desired aesthetical effect. Common ratio values may be, for example, from 1:1.250 to 1:1.500, though more commonly from 1:1.360 and 1:1.500, and with rare occurrences from 1:1.500 and 1:1.618. It should also be understood that when using software tools, such as the M Proportion calculator which will be introduced further on, the M Proportion ratio is not limited to three decimals and may vary in precision depending on the application. For example, FIG. 19 shows an interface (200) for M Proportion calculator in which the M Proportion ratio (208) is precise up to 13 decimals, i.e. 1.3676540544138.

Computing the position of the side positioning lines

As mentioned above, the central positioning line (6) is placed in the center of the smile and dentition (10) and the last side positioning line (0) is positioned by the user, advantageously on the buccal face of the first molar (16), the remaining side positioning lines (5, 4, 3, 2, 1) being computed using the M Proportion for a given ratio. The side positioning lines (5, 4, 3, 2, 1) may be computed as follows:

$$P(i)=P(i-1)-D/F_1, i=1 \text{ to } n-2; \quad \text{Equation 2}$$

where n is the number of positioning lines;
P(i) is the position of positioning line(i), i=0. to n−1;
P(0) and P(n−1) are given;
D is the distance between positioning lines (0) and (n−1), i.e. [P(0)−P(n−1)];

$$F_1 = \Sigma_{j=0}^{n-2} R^1; \quad \text{Equation 3}$$

$$F_i = F_{i-1}/R; \text{ and} \quad \text{Equation 4}$$

R is the ratio of the M Proportion;
which in the context of FIG. 4 translates to:
P(1)=P(0)−D/$F_1$;
P(2)=P(1)−D/$F_2$;
P(3)=P(2)−D/$F_3$;
P(4)=P(3)−D/$F_4$; and
P(5)=P(4)−D/$F_5$;
where:
R, P(0) and P(6) are given;
D=P(0)−P(6); and
$F_1=R^0+R^1+R^2+R^3+R^4+R^5$.

It is to be understood that, as a result of symmetry, Equations 2. to 4. may be adapted for computing the position of positioning lines on the other side of the smile or dentition (10). Furthermore, it is also to be understood that the positioning of side positioning line (0) may be either dependent or independent of the positioning of its corresponding positioning line (00) (see FIG. 4) on the other side of the smile or dentition (10). This is to account for the fact that smiles may not always be perfectly symmetrical or that an image of the patient may not always be perfectly centered.

Figure 5A:
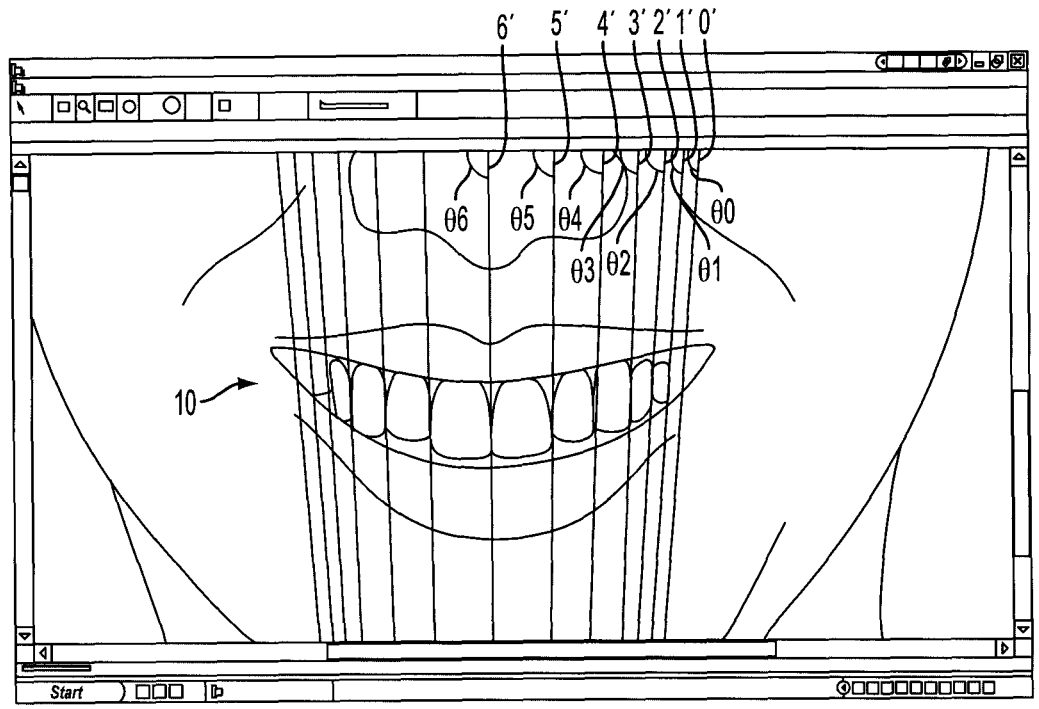
FIGS. 5A and 5B are front views of an image of the smile of an individual on which are superimposed angled positioning lines.
Figure 5B:
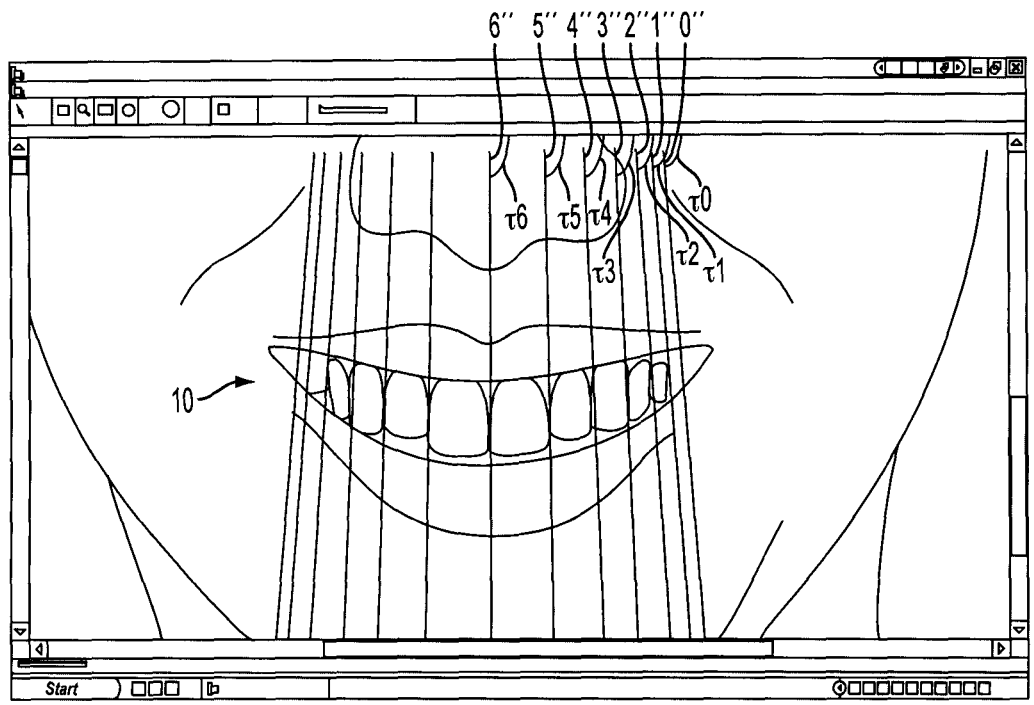

In an alternative embodiments, shown in FIGS. 5A and 5B, the positioning lines (6', 5', 4', 3', 2', 1', 0') may have corresponding angles ($\theta_6$, $\theta_5$, $\theta_4$, $\theta_3$, $\theta_2$, $\theta_1$, $\theta_0$) while positioning lines (6", 5", 4", 3", 2", 1", 0") may have corresponding angles ($\tau_6$, $\tau_5$, $\tau_4$, $\tau_3$, $\tau_2$, $\tau_1$, $\tau_0$) in order to better conform to the natural positioning of the teeth, to address a certain condition such as, for example, occlusion, or for aesthetical reasons. For example, angles of 0, 1.00, 2.00, 2.50, 3.75, 4.40 and 4.50 degrees may be used for angles ($\theta_6$, $\theta_5$, $\theta_4$, $\theta_3$, $\theta_2$, $\theta_1$, $\theta_0$.), respectively. It is to be understood that other angles and that a combination of angles $\theta$ and $\tau$ may also be used.

Measurements

Figure 6:
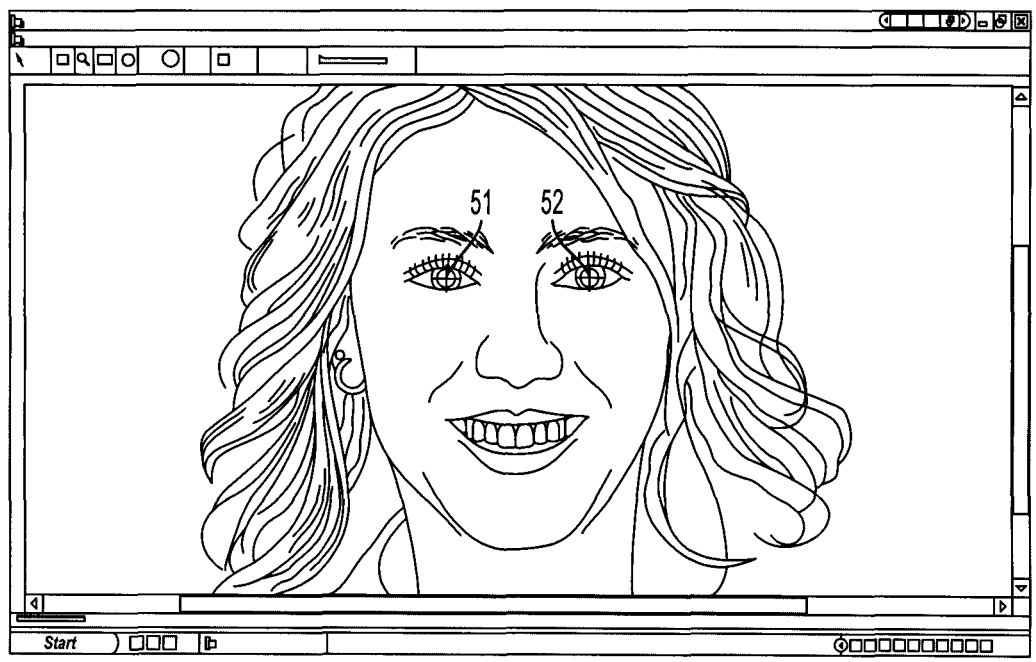
FIG. 6 is a front view image of the smile of an individual on which are superimposed two measurement reference points.
Figure 7:
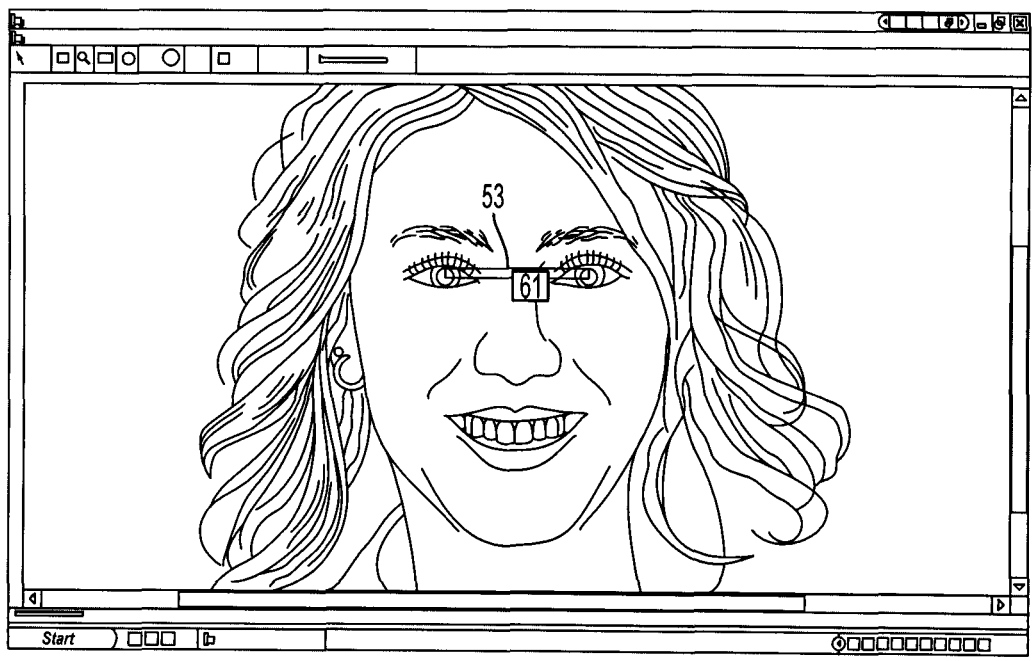
FIG. 7 is a front view image of the smile of an individual on which is superimposed a measuring rule.
Figure 8:
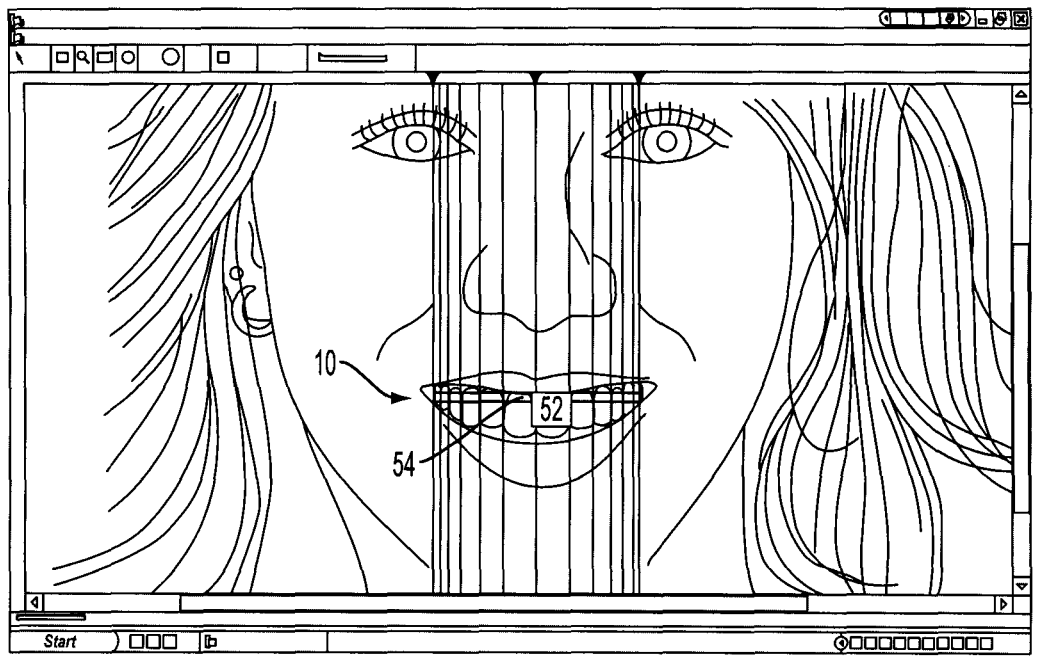
FIG. 8 is a front view image of the smile of an individual on which are superimposed positioning lines following the M Proportion with a ratio of 1:1.367 and a measuring rule.

In order to facilitate the work of the practitioner, reference points (51, 52) on the image of the patient may be identified, as shown in FIG. 6, and the distance (53) separating them inputted into the system, as shown in FIG. 7. In the example of FIGS. 6 and 7, the reference points (51, 52) are positioned at the center of the left and right pupils, respectively, and their distance (53) of 61 mm inputted as a reference. Therefore, using this reference, the measurement of various features on the image of the patient may be computed by relating the inputted distance (53) to the number of pixels between the two reference points (51, 52). For example, as shown in FIG. 8, the patient's inter-molar distance (54) may be computed using the system, in this example the inter-molar distance (54) being 52 mm. In this example, the inter-molar distance is the distance between the buccal faces of the left and right first upper molars (see FIG. 18A for the identification of the first upper molars (116, 16)).

Virtual diagnostic wax-up

Figure 9:
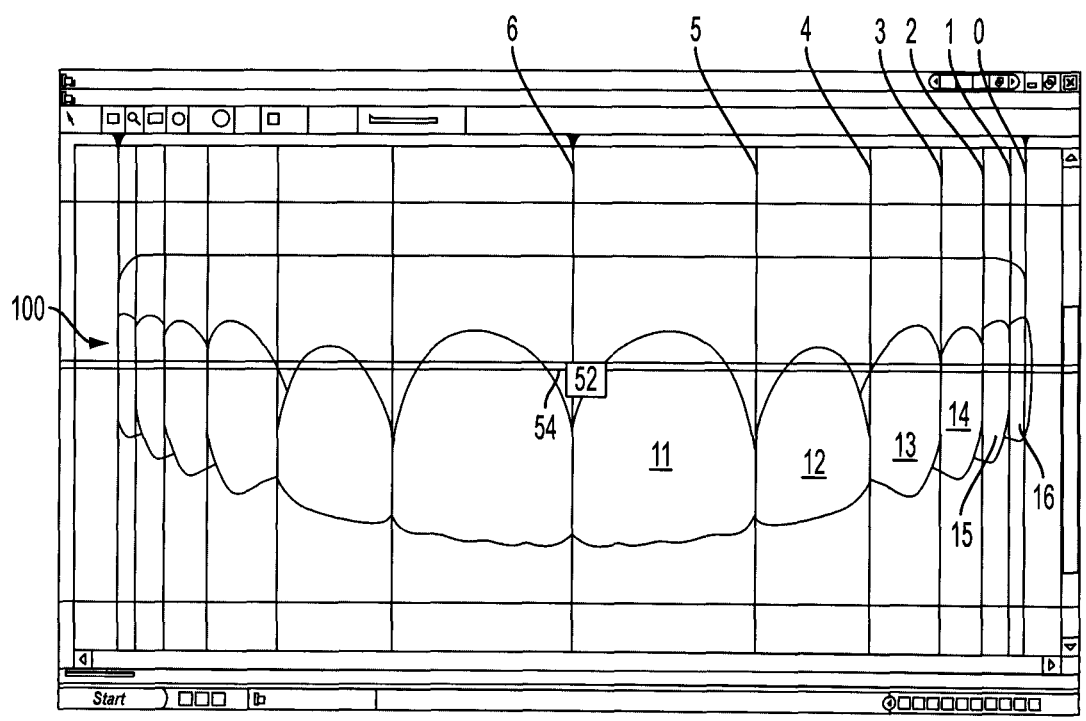
FIG. 9 is a front view image of the dentition of a virtual diagnostic wax-up on which are superimposed positioning lines following the M Proportion with a ratio of 1:1.367.
Figure 10:
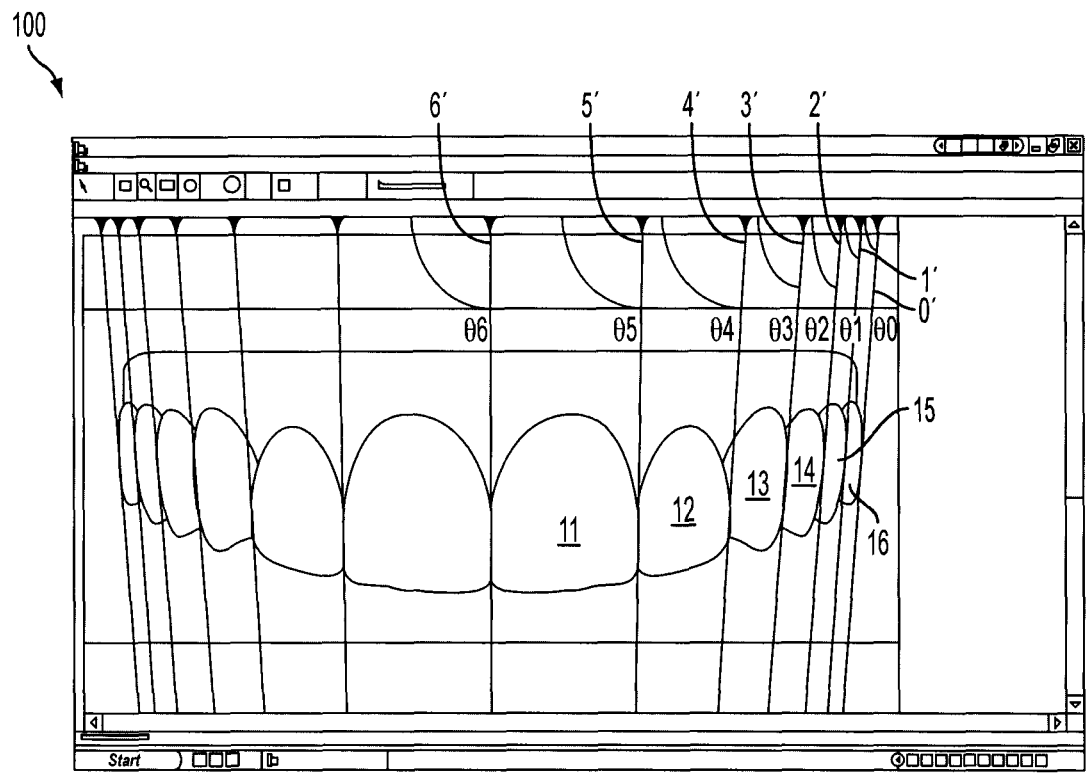
FIG. 10 is a front view image of the dentition of a virtual diagnostic wax-up on which are superimposed angled positioning lines following the M Proportion with a ratio of 1:1.367.

Referring to FIG. 9, the practitioner may use the measurement of the inter-molar distance (54) or the measurement of the central width to create a virtual diagnostic wax-up (100) using the positioning lines (6, 5, 4, 3, 2, 1, 0) as guidelines as to the size and positioning of the teeth (11, 12, 13, 14, 15, 16). In an alternative embodiment, shown in FIG. 10, angled positioning lines (6', 5', 4', 3', 2', 1', 0') may also be used. It is to be understood that although not shown, angled positioning lines (6", 5", 4", 3", 2", 1", 0"), as illustrated in FIG. 5B, may also be used.

The image of the virtual diagnostic wax-up (100) may then be superimposed on the image of the patient and properly scaled so as to be able to view its appearance as a replacement to the patient's dentition (10). If the practitioner wishes to make changes to the virtual diagnostic wax-up (100) he may make measurements directly on the image.

Once the practitioner is satisfied with the aesthetics of the virtual diagnostic wax-up (100), he may then use the measurements thus obtained to create a real diagnostic wax-up.

It is to be understood that the virtual diagnostic wax-up (100) and the M Proportion may be included as part of a CAD CAM, modeling or re-modeling software using, for example, 2D or 3D models, X-Rays or CT scans of a patient's mouth to dispose the teeth when creating, for example, ceramic teeth, orthodontic molds, dentures, etc.

Real diagnostic wax-up

Figure 12:
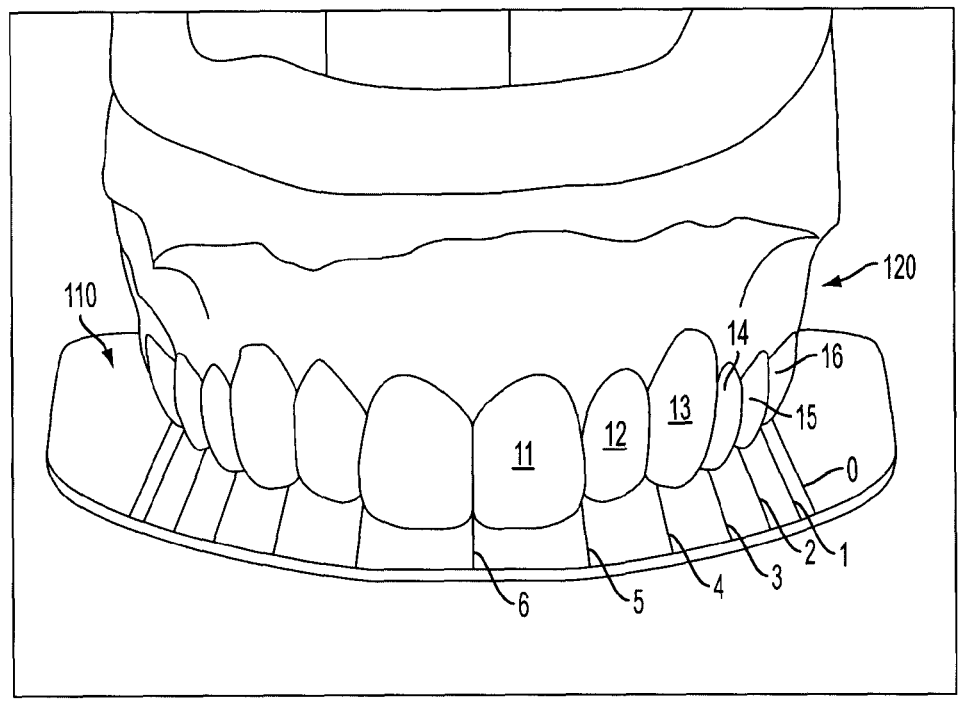
FIG. 12 is a front view image of the smile of a diagnostic wax-up positioned on top of a diagnostic grid on which are superimposed positioning lines following the M Proportion with a ratio of 1:1.38.

The practitioner may use an image of the real diagnostic wax-up, such as the one shown in FIG. 12, and superimpose it on the image of the patient, properly scaled according to the inter-molar distance (54) or the central width measured on the image of the patient, in order to view the real wax-up in the patient mouth. It is to be understood that real diagnostic wax-up created by other processes such as, for example, laboratory work, may be so viewed, not only those created from the virtual diagnostic wax-up.

Diagnostic grid

Figure 11:
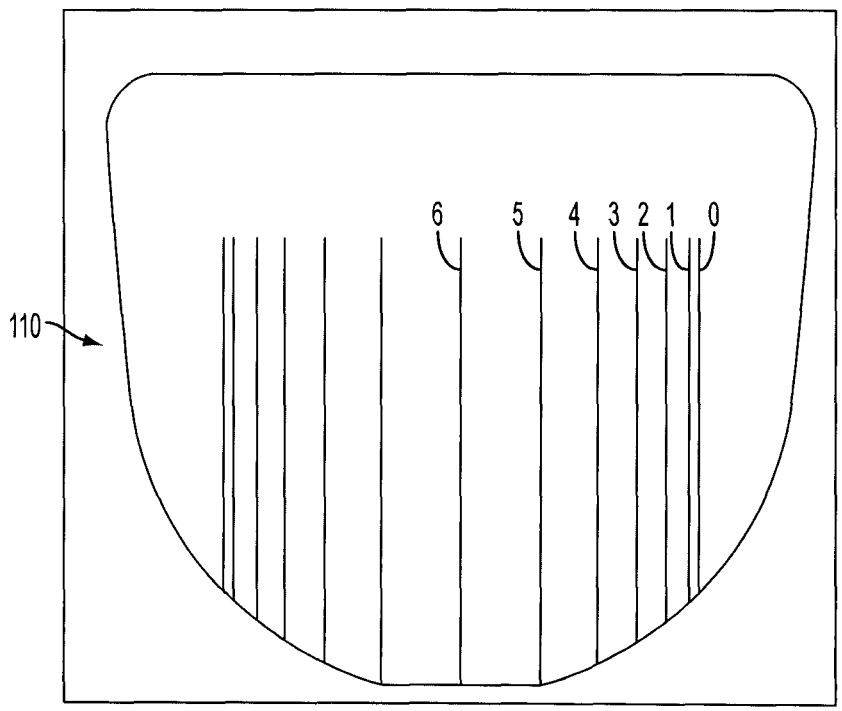
FIG. 11 is a plan view of a diagnostic grid used for laboratory work on which are superimposed positioning tines following the M Proportion with a ratio of 1:1.38.

Referring to FIG. 11, there is shown a plan view of a diagnostic grid (110) on which is applied the M Proportion (ratio of 1:1.38) with seven positioning lines, resulting in a center positioning line (6) and six side positioning lines (5, 4, 3, 2, 1, 0). The diagnostic grid (110) may be made of a material such as, for example, plastic, paper, cardboard, plasticized paper, metal, etc.

Referring now to FIG. 12, a diagnostic wax-up (120) may be positioned on top of the diagnostic grid (110) and the positioning lines (6, 5, 4, 3, 2, 1, 0) may be used as guidelines as to the size and positioning of the teeth (11, 12, 13, 14, 15, 16) of the diagnostic wax-up (120). The diagnostic grid (110) may also be used, for quality control, to diagnose a case, to treatment plans, to verify a diagnostic wax-up (120) created from measurements obtained from the virtual diagnostic wax-up (100), from measurements obtained from the image of the patient such as shown in FIG. 8, measurements obtained directly on the patient or from model casts of his teeth.

Figure 13:
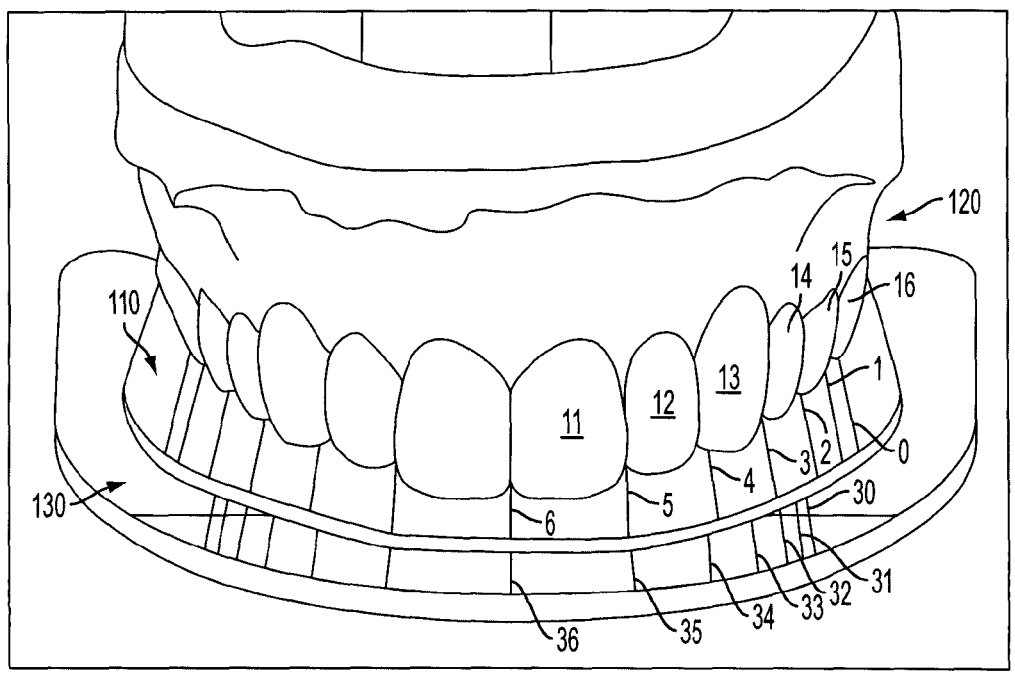
FIG. 13 is a front view image of the dentition of a diagnostic wax-up positioned on top of a diagnostic grid on which are superimposed positioning lines following the M Proportion with a ratio of 1:1.38 and a common diagnostic grid on which are superimposed positioning lines following a Golden Proportion with a ratio of 1:1.618.

Referring to FIG. 13, there is shown, for comparison purposes, the wax-up (120) and diagnostic grid (110) of FIG. 12, the diagnostic grid (110) following M Proportion ratio of 1:1.38, under which is placed a conventional diagnostic grid (130) following a standard Golden Proportion ratio of 1:1.618. As it may be observed, the first three positioning lines (6, 5, 4) of diagnostic grid (110) and the first three positioning lines (36, 35, 34) of conventional diagnostic grid (130) generally correspond to the positioning of the central incisor (11) and the lateral incisor (12). However, it may also be observed that the remaining positioning lines (3, 2, 1, 0) of diagnostic grid (110) generally correspond to the positioning of the canine (13), the first premolar (14), the second premolar (15) and the first molar (16) while the remaining positioning lines (33, 32, 31, 30) of conventional diagnostic grid (130) do not at all. it is apparent that in order to follow the Golden Proportion, the maxillary arch would need to be very narrow.

Figure 14:
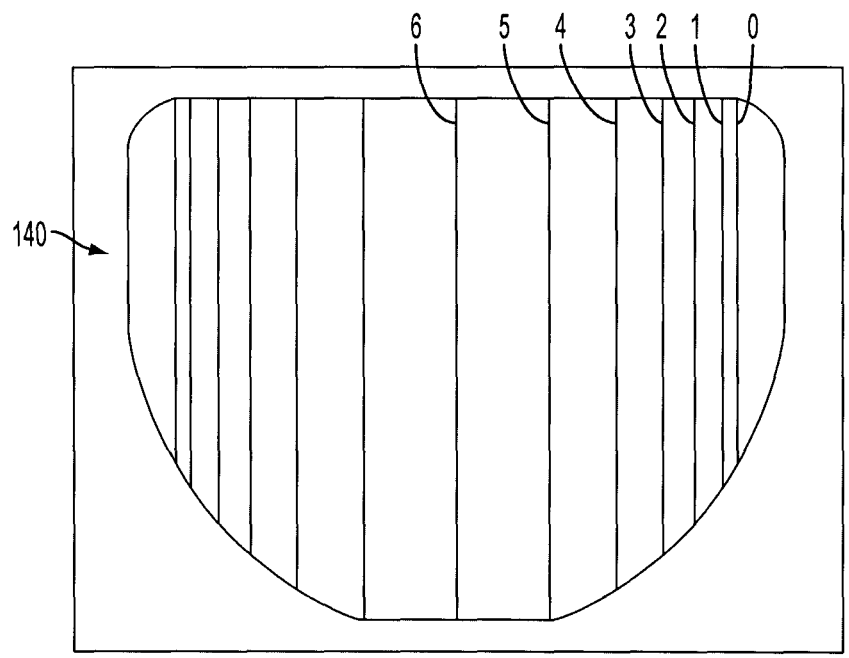
FIG. 14 is a plan view of an alternative diagnostic grid for use in an individual's mouth on which are superimposed positioning lines following the M Proportion with a ratio of 1:1.38.
Figure 15:
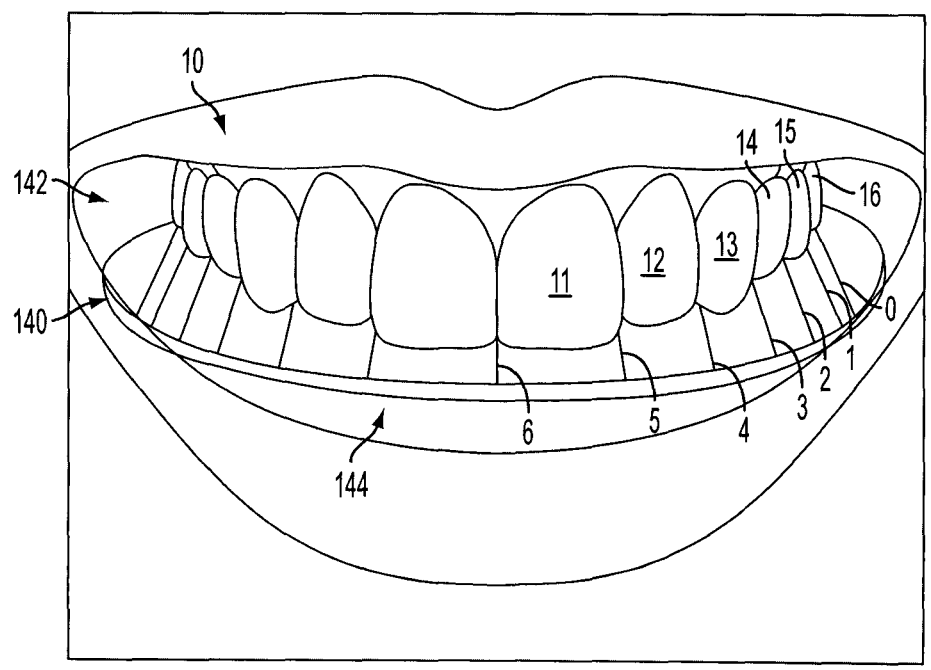
FIG. 15 is a front view image of the smile of an individual with the alternative diagnostic grid, on which are superimposed positioning lines following the M Proportion with a ratio of 1:1.38, positioned between his or her upper and lower teeth.

In an alternative embodiment shown in FIG. 14, a diagnostic grid (140), following M Proportion ratio of 1:1.38, may have a configuration and dimensions suited for insertion in the mouth of a patient. Referring now to FIG. 15, the practitioner may position the diagnostic grid (140) between the upper (142) and lower (144) teeth of a patient and use positioning lines (6, 5, 4, 3, 2, 1, 0) as guidelines as to the positioning of the teeth (11, 12, 13, 14, 15, 16). The practitioner may then establish a diagnostic regarding the dentition (10) of the patient.

In a further alternative embodiment, the diagnostic grid (140) may have some sort of handle or protuberance at the front (not shown) so as to permit easy insertion and removal of the diagnostic grid (140) from the patient's mouth.

In typical applications the diagnostic grids (110, 140) may be created with a specific central incisor (11) width, i.e. distance between positioning lines (6) and (5), and a specific M Proportion ratio, the placement of the other positioning lines (4, 3, 2, 1, 0) being set using the selected M Proportion ratio and central incisor (11) width. For example, the width of the central incisor (11) may typically vary from 7.5 mm to 10 mm in increments of 0.5 mm and the M Proportion ratio may vary from 1:1.36 to 1:1.44 in increments of 0.01, it is understood that more precise in paper. It is to be understood, however, that other values may be used for the central incisor (11) as well as other M Proportion ratios as previously disclosed. It is to be understood that the above described diagnostic grids are based on the width of the central incisor (11) and a given ratio and that more precise diagnostic grids may be created by using M Proportion calculator, which will be described further below. These more precise diagnostic grids may also be printed directly on paper, as will be seen below.

M Proportion calculator

As previously mentioned, the M Proportion may be included as part of a modeling and/or re-modeling software or system using, for example, 2D or 3D models, images, X-Rays or CT scans of a patient's mouth to dispose the teeth when creating, for example, ceramic teeth, orthodontic molds, dentures, etc.

To this end, with reference to FIG. 4, Equations 2, 3 and 4 may be adapted and incorporated into a modeling and/or re-modeling software or system to calculate the position of Y axis side positioning lines (5, 4, 3, 2, 1, 0) from information inputted by the user of the software or system and position them onto a 2D or 3D model, image, X-Ray or CT scan of a patient's mouth, or even print them on some supporting media. In particular, the position of the side positioning lines (5, 4, 3, 2, 1, 0) may be computed from inputting at least two quantities such as, for example, a ratio, i.e. M Proportion ratio, an inter-molar distance and a central incisor width. The various quantities may be inputted either from a user interface, such as, for example, a keyboard, a configuration file, by dragging and positioning the positioning lines (6, 5, 4, 3, 2, 1, 0) or by using some software tool or interface.

Figure 16A:
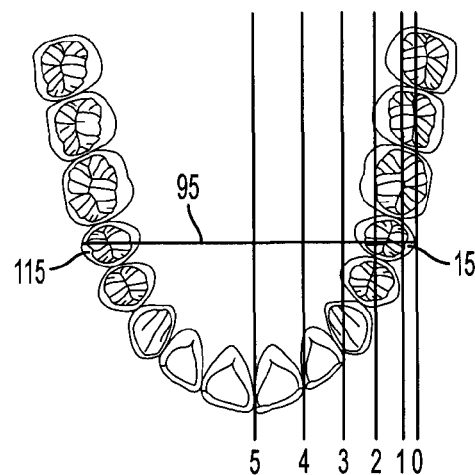
FIGS. 16A, 16B and 16C are bottom views of the upper teeth of an individual on which are superimposed positioning lines with an associated inter-molar distance.

The molars used for the measurement of the inter-molar distance may vary depending on the number of positioning lines used, i.e. depending on the number of teeth that may be seen in the smile of the patient. For example, referring to FIGS. 16A, 16B and 16C, in the case where six positioning lines (5, 4, 3, 2, 1, 0) are used (FIG. 16A) the inter-molar distance (95) is taken between the two second premolars (15, 115), in the case where seven positioning lines (6, 5, 4, 3, 2, 1, 0) are used (FIG. 16B), the inter-molar distance (96) is taken between the two first molars (16, 116) and in the case where eight positioning lines (7, 6, 5, 4, 3, 2, 1, 0) are used (FIG. 16C), the inter-molar distance (97) is taken between the two second molars (17, 117). In another example (not shown), four or five positioning lines may be used, in which case the inter-molar distance would be taken between the canine and first premolars, respectively.

Figure 16B:
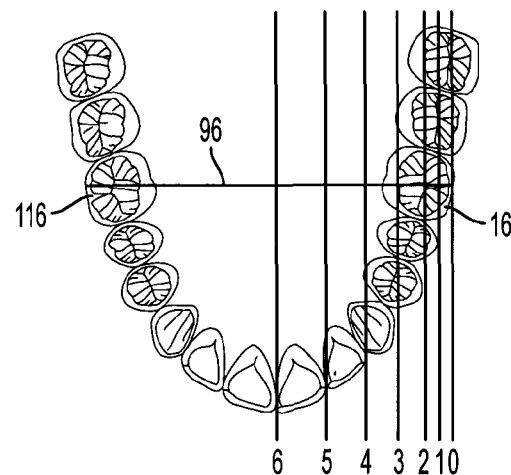
Figure 16C:
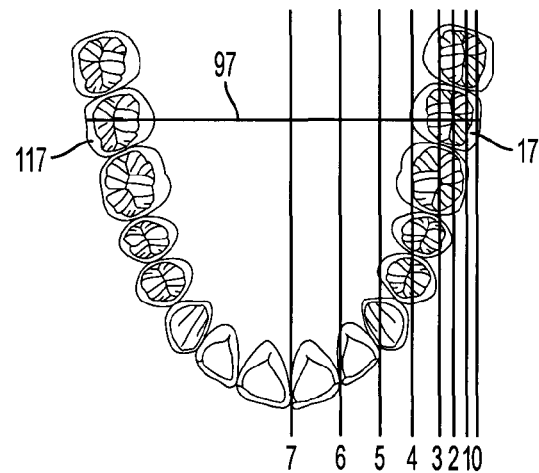

It is to be noted, however, that although reference will be made to FIG. 16B, in which there are seven positioning lines (6, 5, 4, 3, 2, 1, 0), this is for illustrative purpose only and the following discussion may similarly apply to other numbers of positioning lines. Accordingly, for the sake of clarity, the discussion will focus on the use of seven positioning lines (6, 5, 4, 3, 2, 1, 0) while the procedures will be presented such as to be applicable to varying numbers of positioning lines.

In a first non-restrictive embodiment, the position of the side positioning lines (5, 4, 3, 2, 1, 0), referred to as LinePosition(i) where i is the numeral identifying the positioning line, may be calculated from inputting M Proportion ratio, referred to as Ratio, and an inter-molar distance (96), referred to as InterMolarDistance and applying the procedure "CentralIncisorWidth". It is to be understood that in the example of FIG. 16B with seven positioning lines, the variable #OfLines, which represents the number of positioning lines, will be equal to seven. As for the inter-molar distance (96), it will be measured between the two first molars (16, 116). It should be noted that in addition to calculating the position of the side positioning lines (5, 4, 3, 2, 1, 0), the procedure also provides the central incisor width.

Calculate Central Incisor Width

```
CentralIncisorWidth (Ratio, #OfLines, InterMolarDistance)
    LinePosition (#OfLines − 1) = InterMolarDistance / 2
    LinePosition (0) = 0
    Constant (1) = GetFirstPhi (Ratio, #OfLines − 2)
    For i = 2 to #OfLines − 2
        Constant (i) = Content (i−1) / Ratio
    Next i
    For i = 1 to #OfLines − 2
        LinePosition (i) = (LinePosition (#OfLines − 1) −
                          LinePosition (0)) / Constant (i) −
                          LinePosition (i−1)
    Next i
    CentralIncisorWidth = LinePosition (i−1) − LinePosition (i−2)
    RETURN CentralIncisorWidth
GetFirstPhi (Ratio, #OfLines−2)
    For n = 1 to #OfLines − 2
        GetFirstPhi = GetFirstPhi + (Ratio ^ n)
    Next n
    GetFirstPhi = GetFirstPhi + 1
    RETURN GetFirstPhi
```

In a second non-restrictive embodiment, the position of the side positioning lines (5, 4, 3, 2, 1, 0), referred to as LinePosition(i) where i is the numeral of the positioning line, may be calculated from inputting M Proportion ratio, referred to as Ratio, and a central incisor (11) width, referred to as CentralIncisorWidth, and applying the procedure "InterMolarDistance". It is to be understood that in the example of FIG. 16B with seven positioning lines, the variable #OfLines, which represents the number of positioning lines, will be equal to seven. It should be noted that in addition to calculating the position of the side positioning lines (5, 4, 3, 2, 1, 0), the procedure also provides the inter-molar distance (96), which is the distance between the two first molars (16, 116).

Calculate Inter-molar Distance

```
InterMolarDistance (Ratio, #OfLines, CentralIncisorWidth)
    LinePosition (#OfLines − 1) = 0
    LinePosition (#OfLines − 2) = LinePosition (#OfLines − 1) −
                                  CentralIncisorWidth
    Calc ( )
    For i = #OfLines − 1 to 0 step −1
        LinePosition (i) = LinePosition (i) − LinePosition (0)
    Next i
    InterMolarDistance = LinePosition (#OfLines − 1) * 2
    RETURN InterMolarDistance
Calc ( )
    For i = #OfLines − 1 to 2 step −1
        LinePosition (i−2) = LinePosition (i−1) − (LinePosition (i) −
                            LinePosition (i−1)) / Ratio
    Next i
```

In a third non-restrictive embodiment, the position of the side positioning lines (5, 4, 3, 2, 1, 0), referred to as LinePosition(i) where i is the numeral of the positioning line, may be calculated from inputting a central incisor (11) width, referred to as CentralIncisorWidth, and an inter-molar distance (97), referred to as InterMolarDistance, and applying the procedure "Ratio". It is to be understood that in the example of FIG. 18B with seven positioning lines, the variable #OfLines, which represents the number of positioning lines, will be equal to seven. It should be noted that in addition to calculating the position of the side positioning lines (5, 4, 3, 2, 1, 0), the procedure also provides the corresponding M Proportion ratio.

Calculate Ratio

```
Ratio (InterMolarDistance, #OfLines, CentralIncisorWidth)
    LinePosition (#OfLines − 1) = InterMolarDistance / 2
    LinePosition (#OfLines − 2) = LinePosition (#OfLines − 1) −
                                  CentralIncisorWidth
    Ratio = 1
    Calc ( )
    p = ratio / 2
    For n = 1 to 100
        If LinePosition (0) < 0 Then
            Ratio = Ratio + p
        Else
            Ratio = Ratio − p
        End If
        Calc ( )
        p = p / 2
    Next n
    RETURN Ratio
```

It is to be understood that in the loop "For n=1 to 100", during the calculation of the M Proportion ratio, the number of times the loop is executed, namely 100, may vary depending on the desired precision of the result and as such, the number of times the loop is executed may be more or less than 100.

Figure 17:
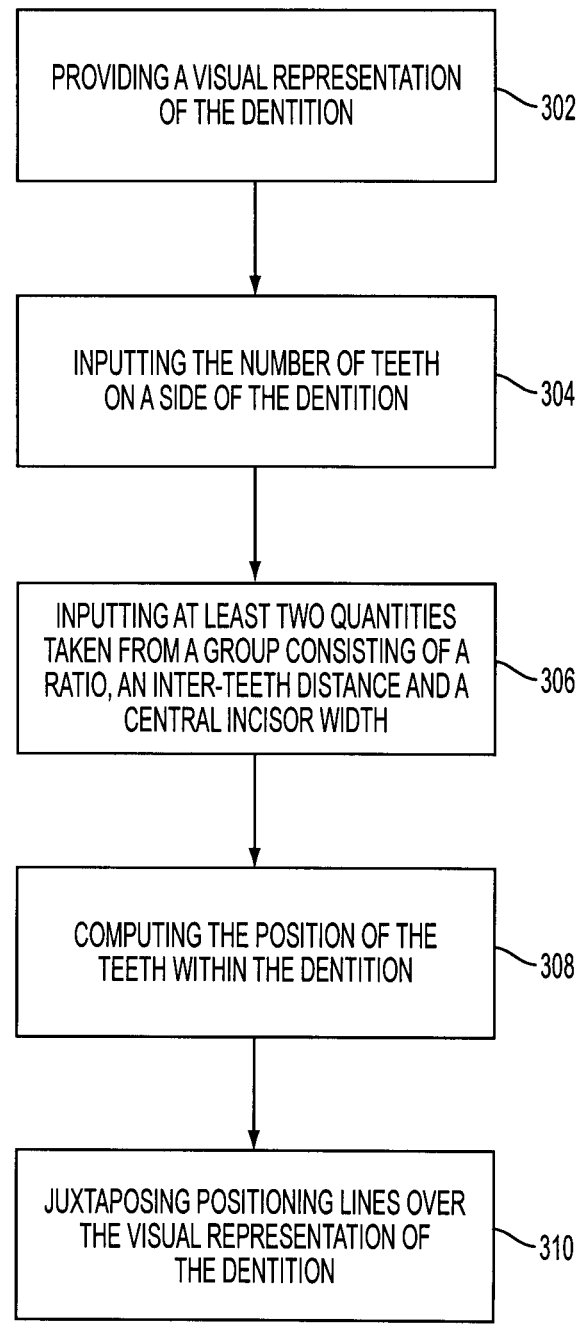
FIG. 17 is a flow diagram depicting the M Proportion calculator process.

Referring now to FIG. 17, there is shown a flow diagram of the M Proportion calculator process. The steps composing the process are indicated by blocks 302 to 310.

The process starts at block 302, where a visual representation of the dentition is provided. Then, at block 304, a value representative of the number of teeth on a side of the dentition is inputted, this value will be used to determine the number of positioning lines, i.e. number of teeth plus one, and between which teeth the inter-molar distance is to be measured.

At block 306, at least two quantities taken from a group consisting of a ratio, an inter molar distance (also referred to as inter-teeth distance because, depending on the value inputted at block 304, the measurement may not necessarily be taken between molars as explained previously) and a central incisor width are inputted.

At block 308, the process computes the position of the positioning lines, which are used to determine the position of the teeth Within the dentition, by applying a mathematical function to the value representative of the number of teeth inputted at block 304 and the quantities inputted at block 306. The mathematical function will be further detailed below.

Finally, at block 310, the positioning lines computed at block 308 are juxtaposed over the visual representation of the dentition.

Figure 18:
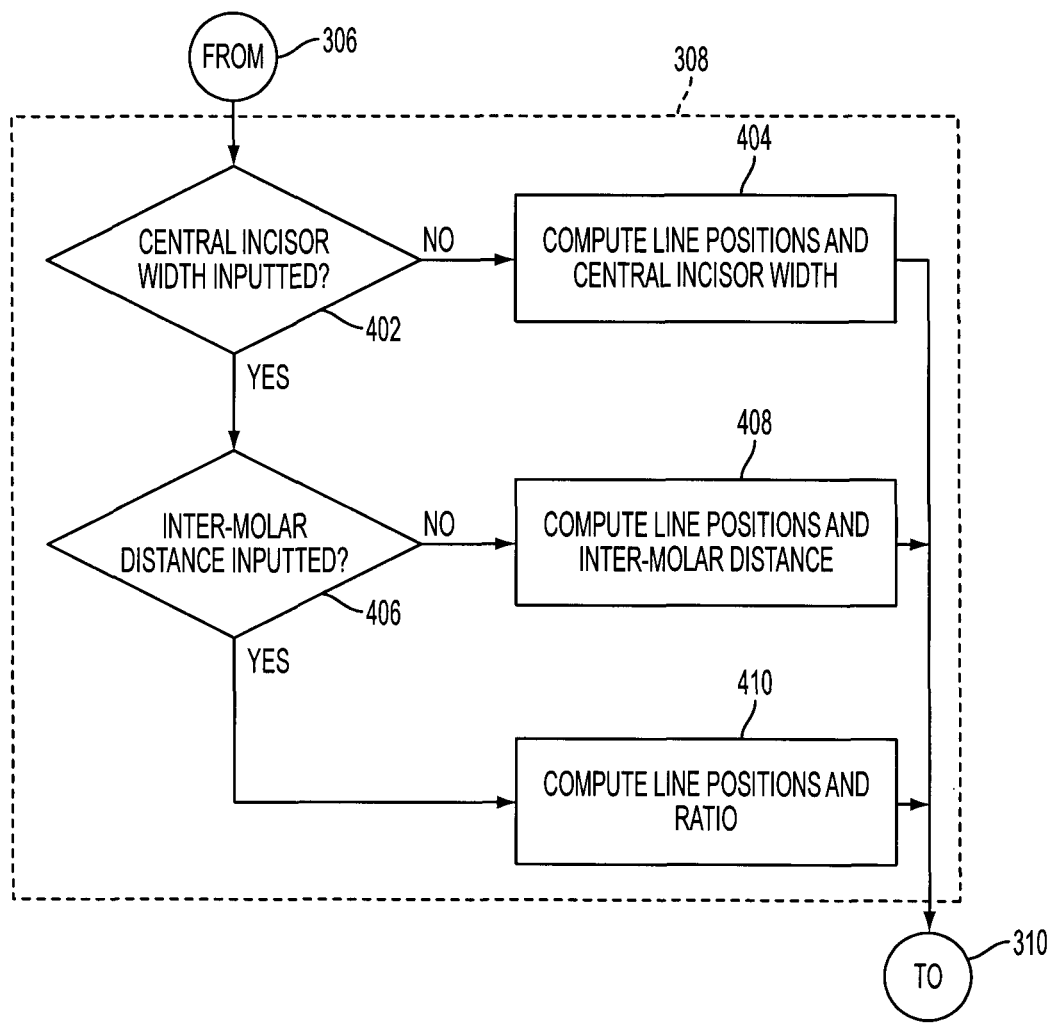
FIG. 18 is a flow diagram depicting teeth position computing step of the M Proportion calculator process of FIG. 17.

Referring to FIG. 18, there is shown flow diagram depicting teeth position computing of block 308 of the M Proportion calculator process described above, The steps composing the process are indicated by blocks 402 to 410.

At block 402, the process verifies if a central incisor width was inputted. If a central incisor width was not inputted, the process executes, at block 404, the CentralIncisorWidth procedure and then proceeds to block 310 of FIG. 19. If a central incisor width was inputted, the process proceeds to block 406.

At block 406, the process verifies if an inter-molar distance was inputted. if an inter-molar distance was not inputted, the process executes, at block 408, the InterMolarDistance procedure and then proceeds to block 310 of FIG. 17. If an inter-molar distance was inputted, the process proceeds to block 410.

At block 410, the process executes the Ratio procedure and then proceeds to block 310 of FIG. 17.

Referring to FIG. 19, there is shown an example of an interface (500) that may be used with the M Proportion calculator. A first (502), second (504), third (506) and fourth (508) input boxes may be used to enter the number of lines to be displayed (#OfLines), the central incisor width (CentralIncisorWidth), the inter-molar distance (InterMolarDistance) and the M Proportion ratio (Ratio), respectively. As discussed previously, after the number of lines has been entered in input box (502), which may also be in the form of a scroll down menu, at least two of input boxes (504), (506) and (508) must be filled, i.e. two out of the central incisor width, inter-molar distance and M Proportion ratio must be entered.

To activate the M Proportion calculator, the activation buttons (505), (507) and (509) corresponding the missing quantity is selected. For example, if the central incisor width (504) and inter-molar distance (506) are entered, then activation button (509) is selected. The M Proportion calculator will then use the Ratio procedure to calculate the position of the side positioning lines (5, 4, 3, 2, 1, 0) as well as the M Proportion ratio, which is then displayed in input box (208). It is to be understood that procedures CentralIncisorWidth and InterMolarDistance are similarly used when activation buttons (505) and (507) are selected, respectively.

Figure 22:
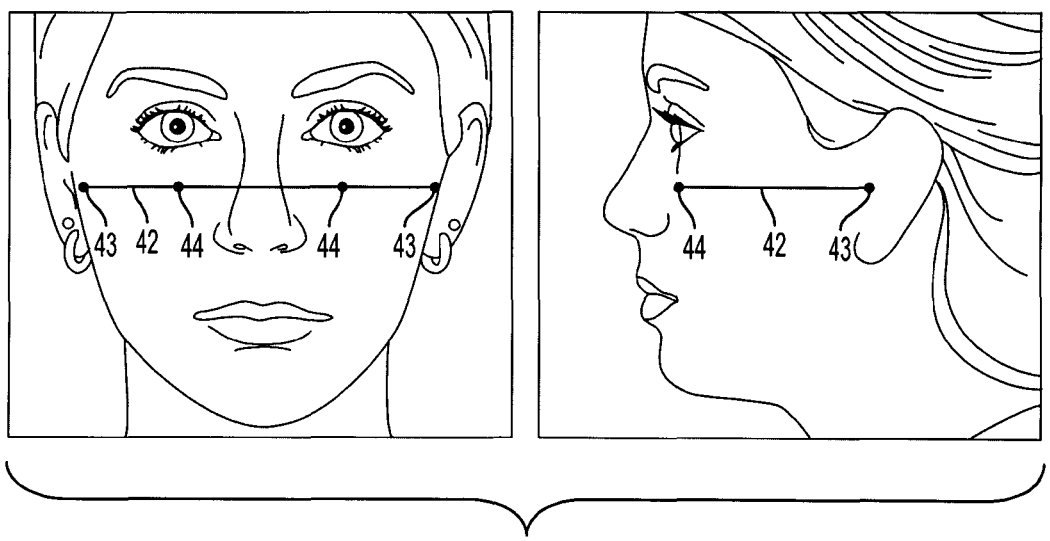
FIG. 22 is as representation of the Frankfurt Plane passing through the Porion and Orbitalis radiological points.

The positioning lines (6, 5, 4, 3, 2, 1, 0) may then be displayed (510) on the M Proportion calculator interface (500) and/or on an image of the patient's dentition (10), as shown in FIG. 22. Furthermore, the interface (500) may have various options such as, for example, the ability to print the positioning lines (6, 5, 4, 3, 2, 1, 0) on a sheet of paper or to create, for example, diagnostic grids such as shown in FIGS. 11 and 14, by selecting the print button (512).

Referring back to FIG. 18, there is shown an example of possible values obtained from the M Proportion calculator with seven lines (input box 502), a central incisor width of 8.25 mm (input box 504), an inter-molar distance of 52 mm (input box 506) and M Proportion ratio of 1.3676540544138 (input box 508). The resulting positioning lines (6, 5, 4, 3, 2, 1, 0) are displayed (510) on the M Proportion calculator interface (500).

Figure 20:
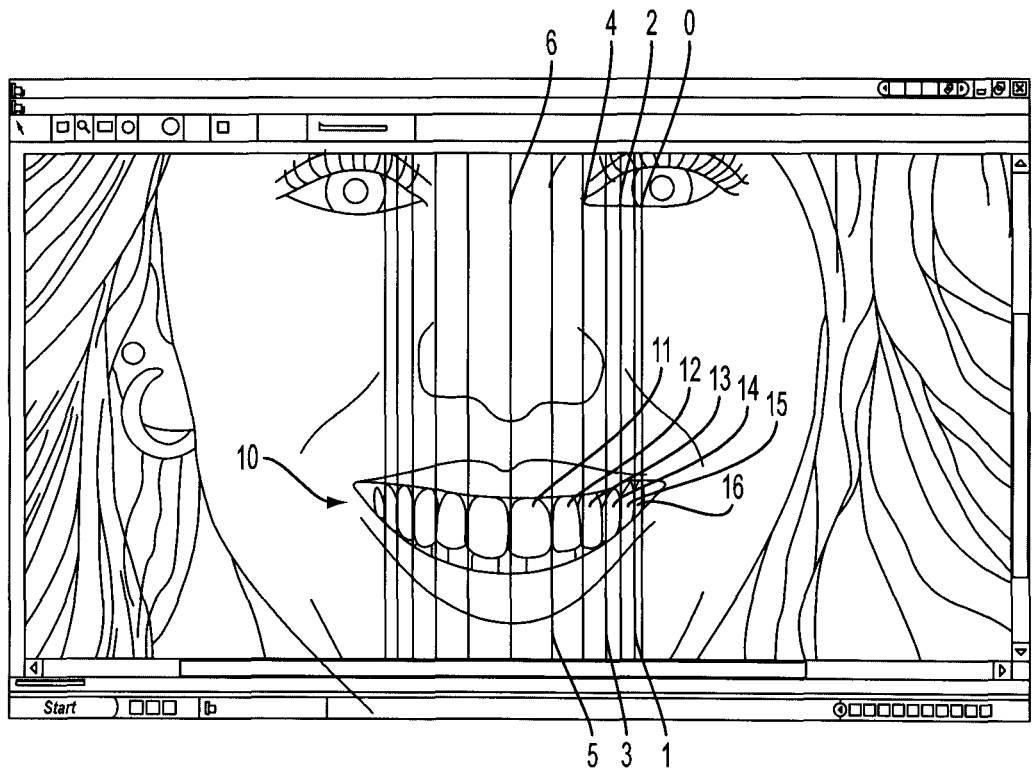
FIG. 20 is a front view image of the smile of an individual having received corrective crowns following the M Proportion shown in FIG. 19.

Referring now to FIG. 20, there is shown representation of an image of the dentition (10) of a patient having received corrective crowns following the M Proportion calculator values displayed in the interface (500) of FIG. 19. It may be observed that the corrected positions of the central Incisor (11), lateral incisor (12), canine (13), first premolar (14), second premolar (15) and first molar (16) are now generally in accordance with the corresponding center positioning line (6) and six side positioning fines (5, 4, 3, 2, 1, 0).

Incorporating an Adjustable M Proportion Ruler in the Virtual Wax-up

Figure 38:
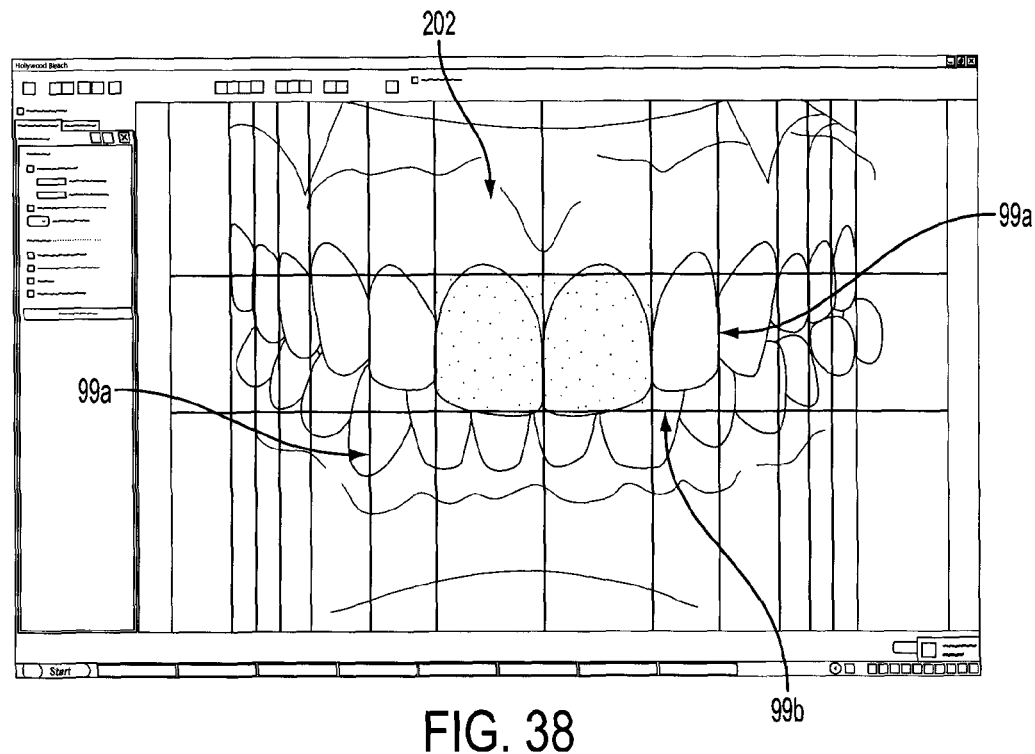
FIG. 38 is an example of a smile in the 3D model library.
Figure 39:
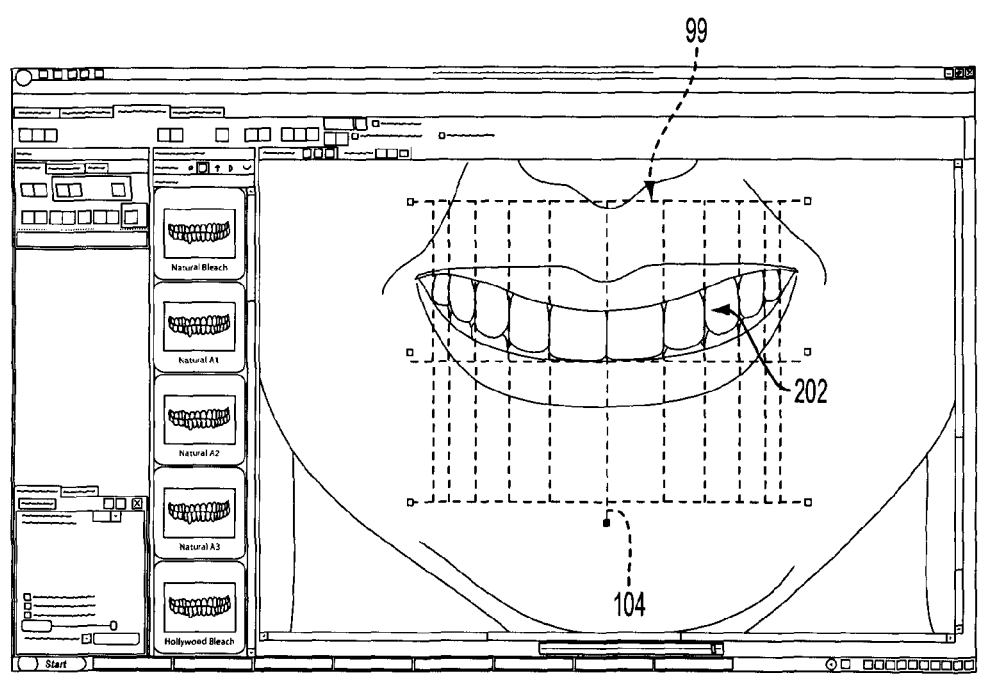
FIGS. 39 and 40 are front view images of the virtual diagnostic wax-up of an individual for two different pitch values.
Figure 40:
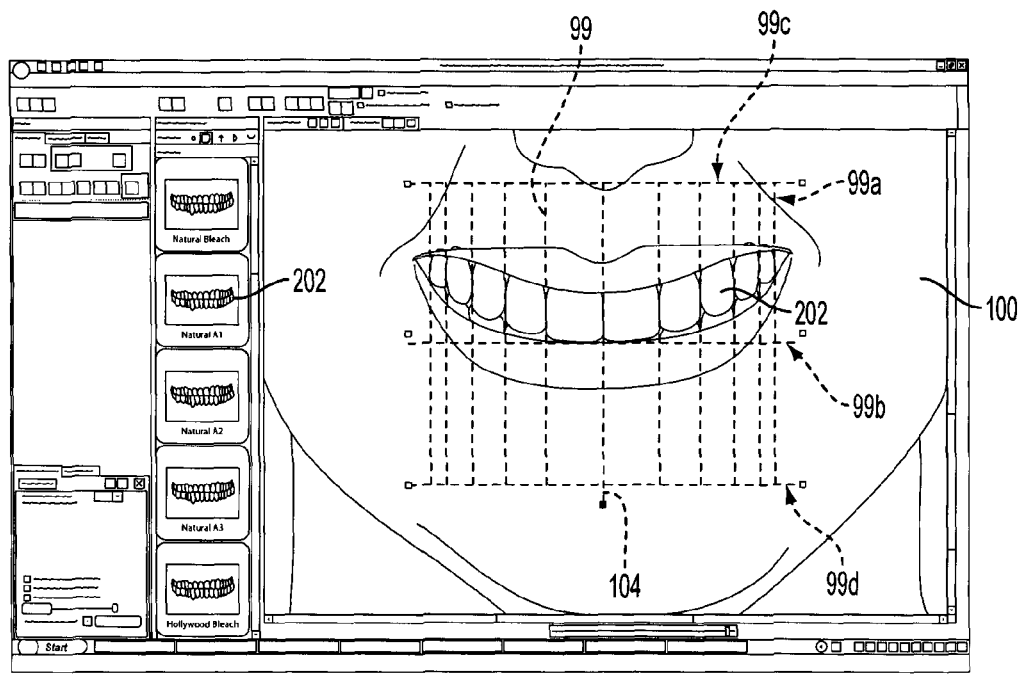

Referring to FIG. 38, the lines of the M Proportion ruler (98) are attached to the each tooth in the teeth library. When clicking on a smile (202) in the library, the M Proportion ruler (98) vertical lines (98a) and the horizontal line (98b) are fused over the patient mouth to the distal part of each tooth and the incisal edge of the centrals, respectively. This results in an immediate virtual wax-up.

Figure 33:
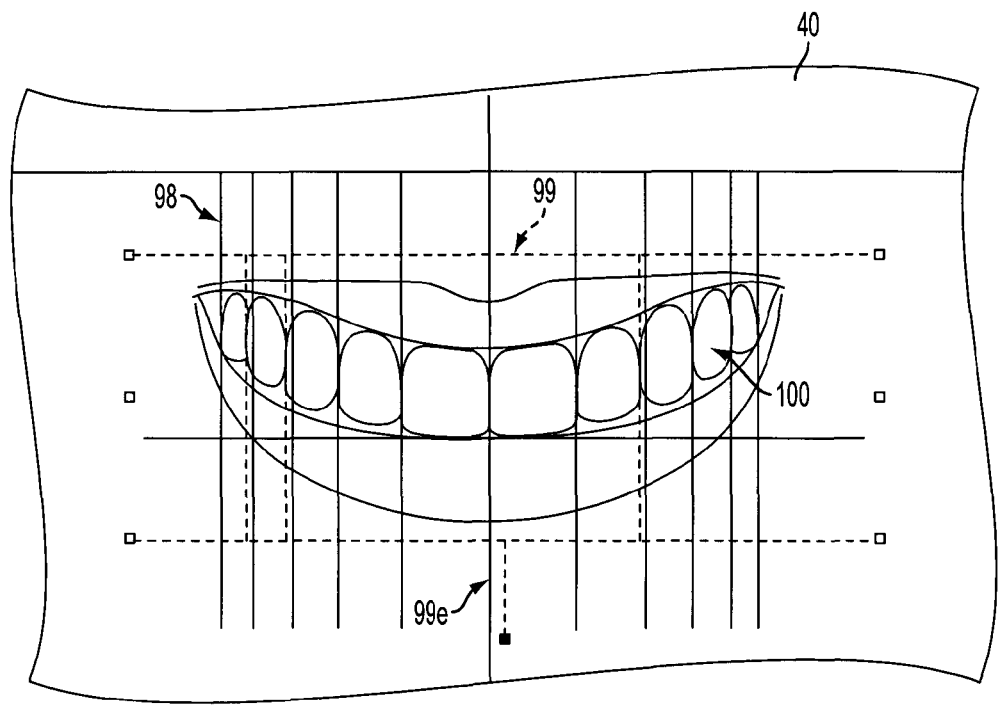
Figure 34:
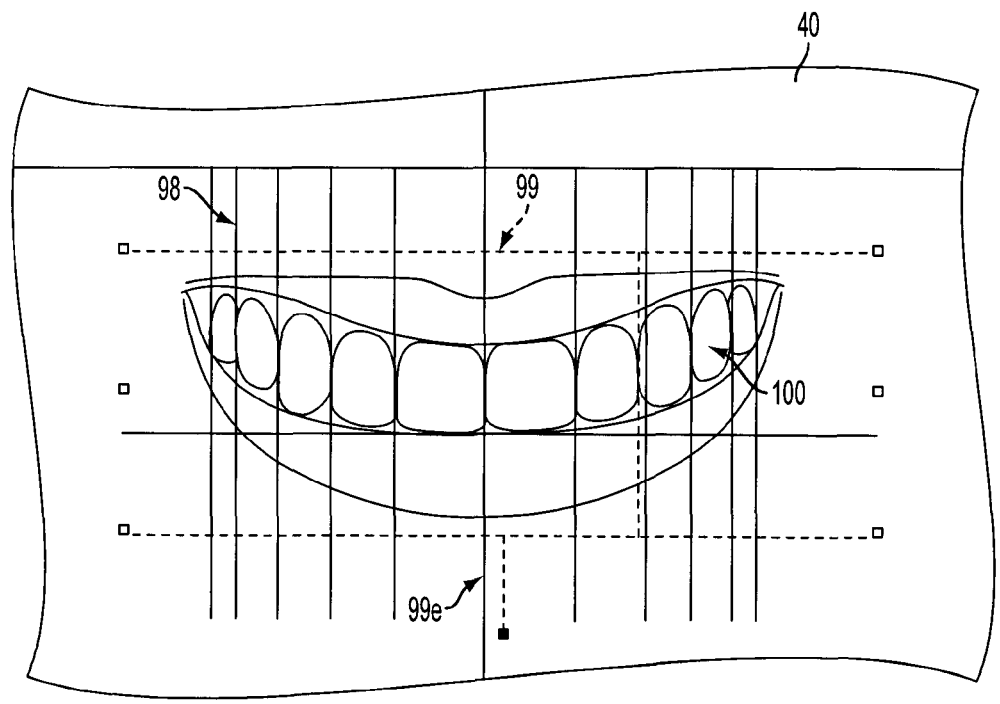
Figure 35:
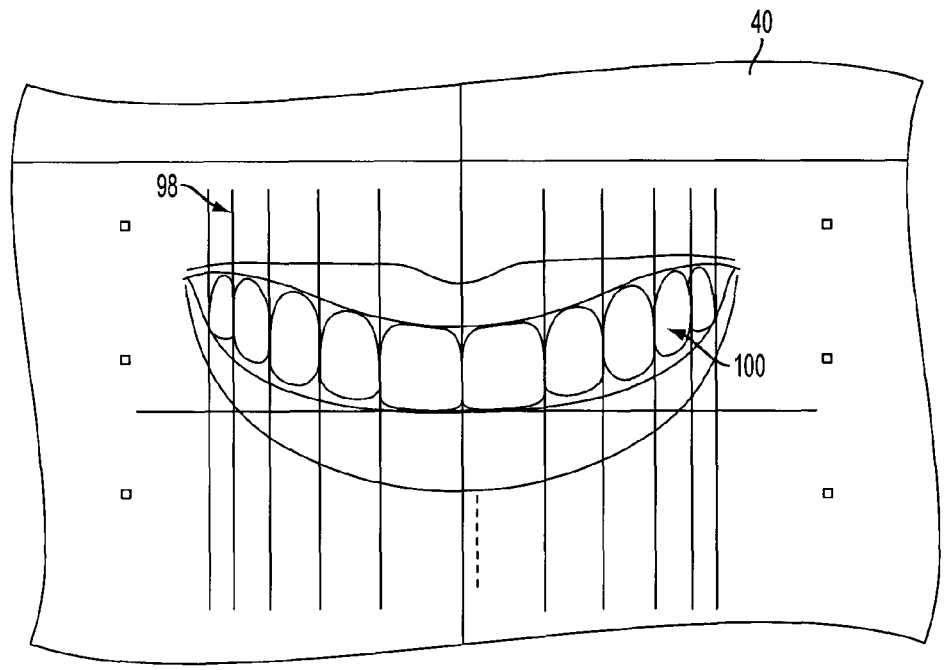

Referring to FIGS. 33 and 34, the adjustable, M Proportion ruler (99) superimposed over the M Proportion ruler (98) enables the displacement of each tooth individually to adapt the virtual wax-up (100) to the pre-op teeth and gum to execute a more accurate virtual wax-up (100).

The M Proportion Ruler

Figure 32:
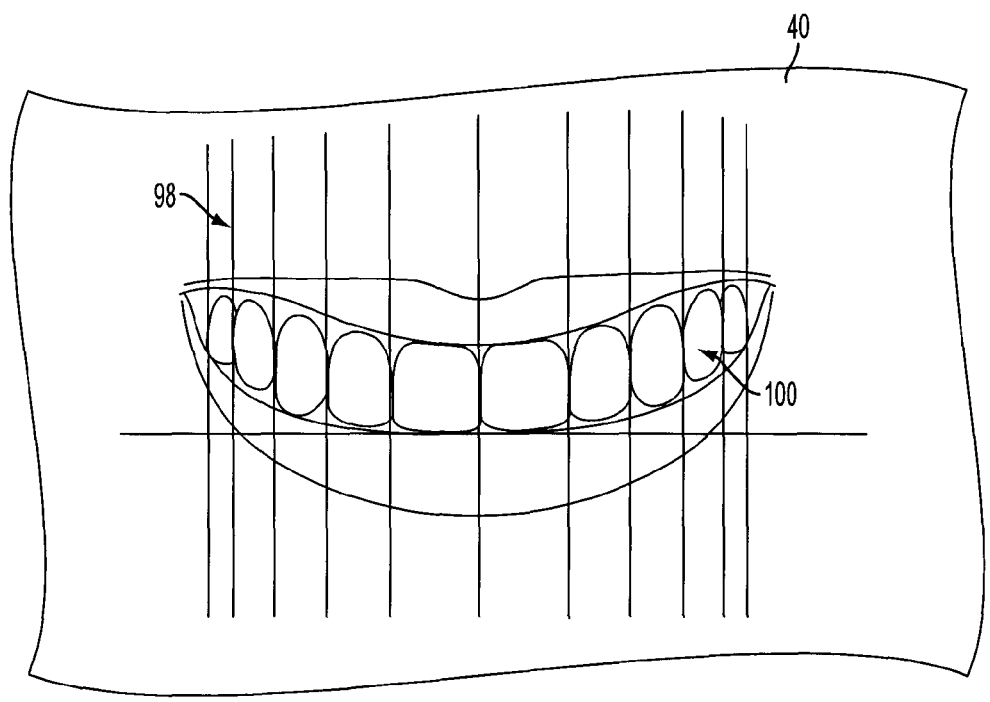

Referring back to FIG. 32, the red lines (98a) between the center and the last lines moves along with the M Proportion calculator values based on the central width, the inter molar width and the M Proportion ratio of the patients mouth. The red lines (98a) cannot be moved individually, they are locked with the values of the M Proportions calculator.

Referring to FIGS. 33 and 34, the center blue line (99e) can move left or right to change the position of the adjustable M Proportion ruler to be able to put the maximum of red lines at the distal part of the maxillary teeth.

The last green lines can be moved through or against the center blue line to bring the green lines of the M Proportion ruler on to the buccal crest of the first molar.

The Adjustable M Proportion Ruler

Each horizontal blue line (99b, 99c, 99d) can be moved up or down:
 the upper horizontal line (99c) moves the ginvigal height;
 the middle horizontal line (99b) moves the incisal edge of all teeth; and
 the lower horizontal line (99d) moves the lower teeth in height By moving both upper and middle horizontal (99c, 99b) lines, this increases or decreases the length of the teeth.

Figure 45:
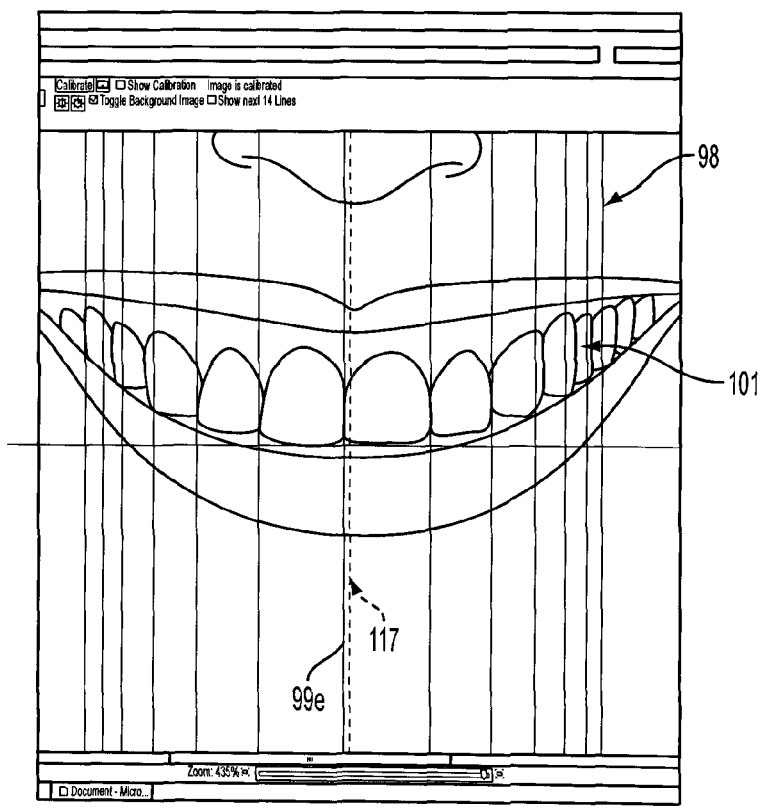
FIGS. 45 to 47 are front view images of the virtual diagnostic wax-up of an individual illustrating the adjustment of the centered line of the adjustable M Proportion ruler to correct midline deviation.
Figure 46:
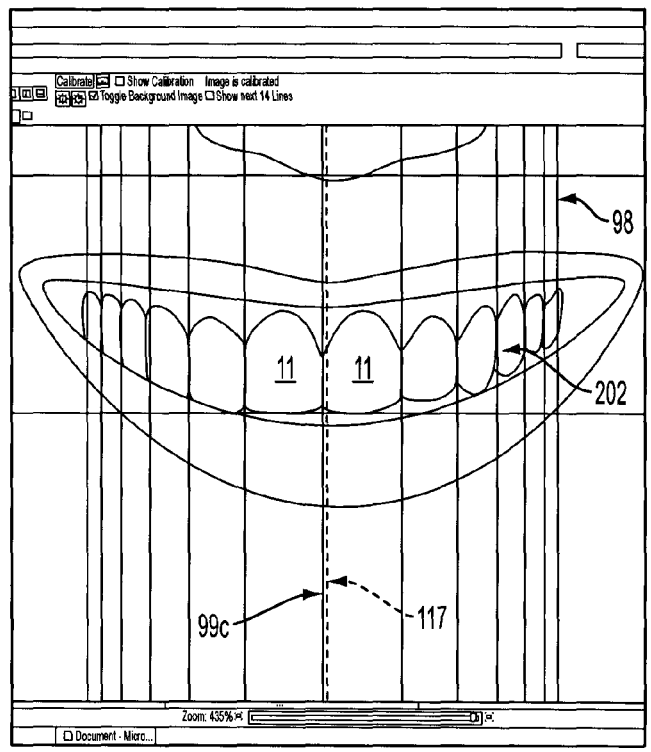
Figure 47:
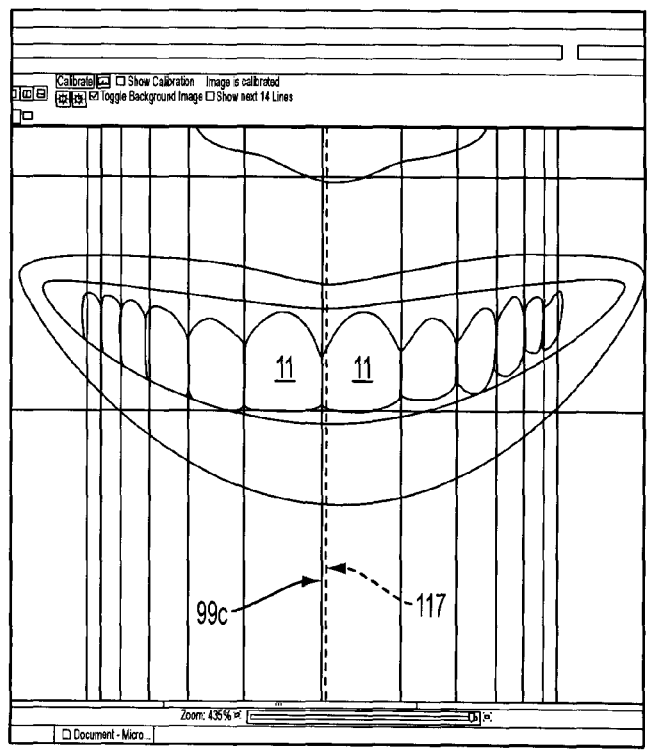

Each vertical blue line (99a), except the centered line, can be moved to the right or to the left to accommodate the pre-op teeth and gum. The centered line is able to move by 1 mm through the facial to correct midline deviation, FIGS. 45 to 47 show the adjustment of the center line (99e) with respect to the midline (117).

The blue square (104) attached to the lower blue horizontal line is a pitch adjustor that moves the posterior teeth in the library on a parabolic curvature when the blue square (104) is moved up or down, thus changing the pitch. This changes the angulation of the occlusal plane in accordance with the smile line.

Figure 41:
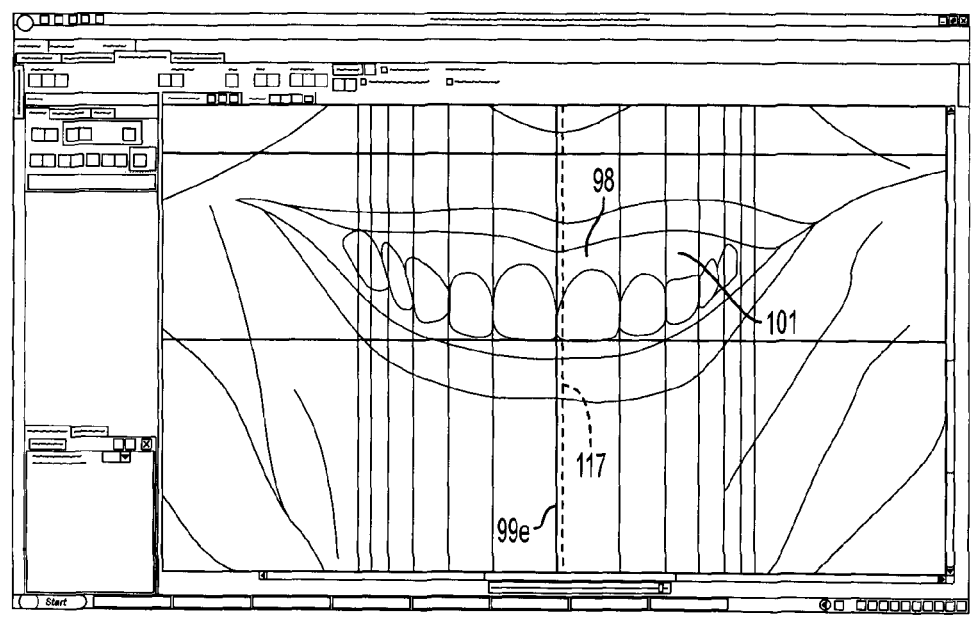
FIGS. 41 to 43 are front view images of the smile of an individual during a virtual gingivectomy.
Figure 42:
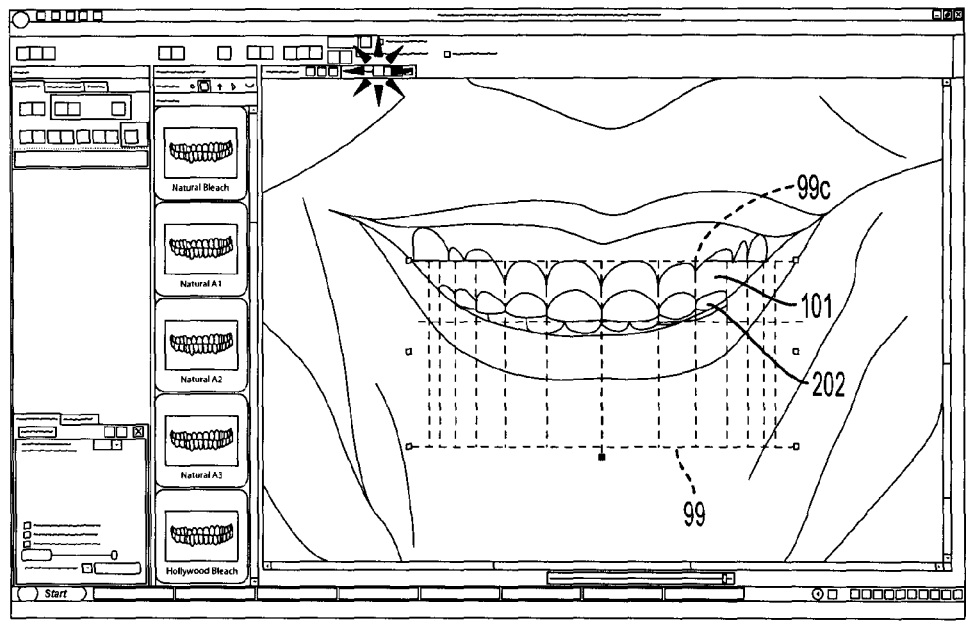
Figure 43:
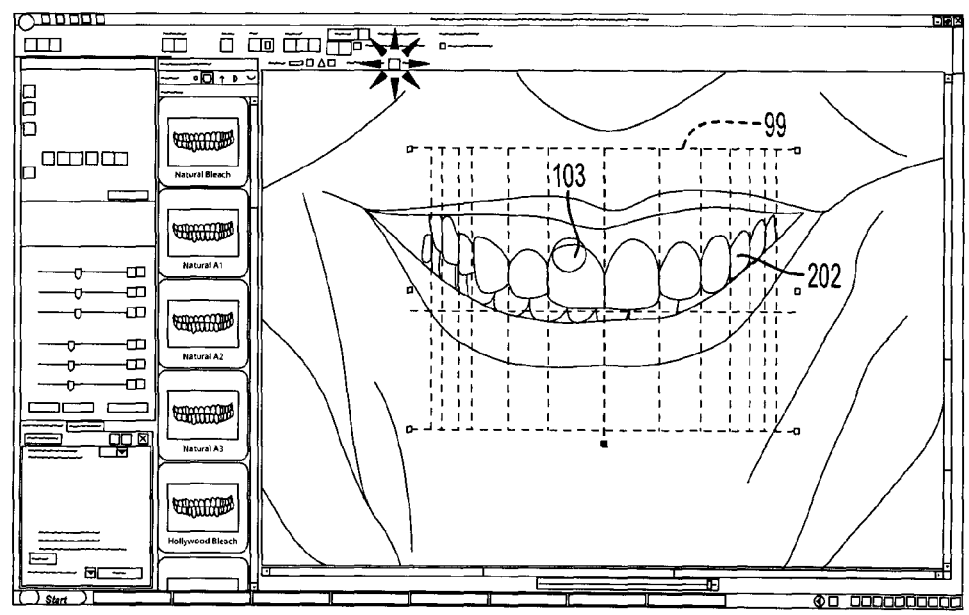

The M Proportion ruler (98) is used to diagnose, and to dispose teeth in their best position in orthodontic treatment, prosthodontic treatment (crowns, bridges, veneers) or for dentures. The adjustable M Proportion ruler (99) in the virtual wax-up (100) is automatically adapted to the horizontal line and the center vertical line of the M Proportion ruler (98) to achieve the best disposition of teeth in the dental arch, Taking in consideration the periodontal tissues of the underneath tooth contour and gum, the virtual wax-up (100) is customized to each mouth (best seen in FIG. 34 at the distal of the left lateral), Gingivectomy Referring to FIGS. 41 to 43, the system allows very accurate gingivectomies. The library smiles (202) slide between the teeth and gum (101) in the patient's mouth on the facial picture. The upper horizontal blue line (99c) of the adjustable M Proportion is pulled up to bring the teeth of the library (202) under the patient's gum (101). A round size adjustable tool (103) allows the gingivectomy by cutting the gum (101) of the patient and showing the underneath tooth or teeth of the library (202).

Digital Facebow Using a 2D Facial Photograph.

Figure 44:
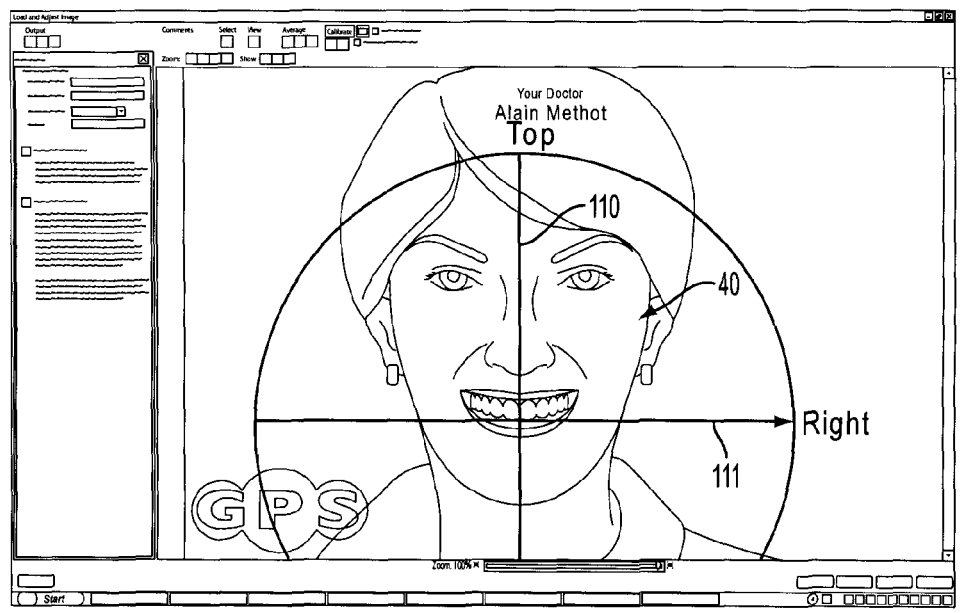
FIG. 44 is a front view image of a patient showing the digital facebow alignment procedure.

Referring to FIG. 44, a part of the digital facebow is in the rotation application that positions the long axis of the face perpendicular to the floor. This application set up the position of the patient face (40) on the articulator. The long axis is usually used as the standard position but the upper lip line or inter papillary line can be used.

When aligning the vertical line (110) to the long axis of the face the intersection of both horizontal (111) and vertical (110) lines are brought at the intersection of the incisal edges of the upper centrals and the dental midline of the upper centrals on the image (40). The horizontal line (111) is apposed at the incisal edges of the upper centrals and is perpendicular to the vertical line (110) passing through the dental midline. The intersection of the vertical and horizontal line is pivot of the digital facebow.

Figure 21:
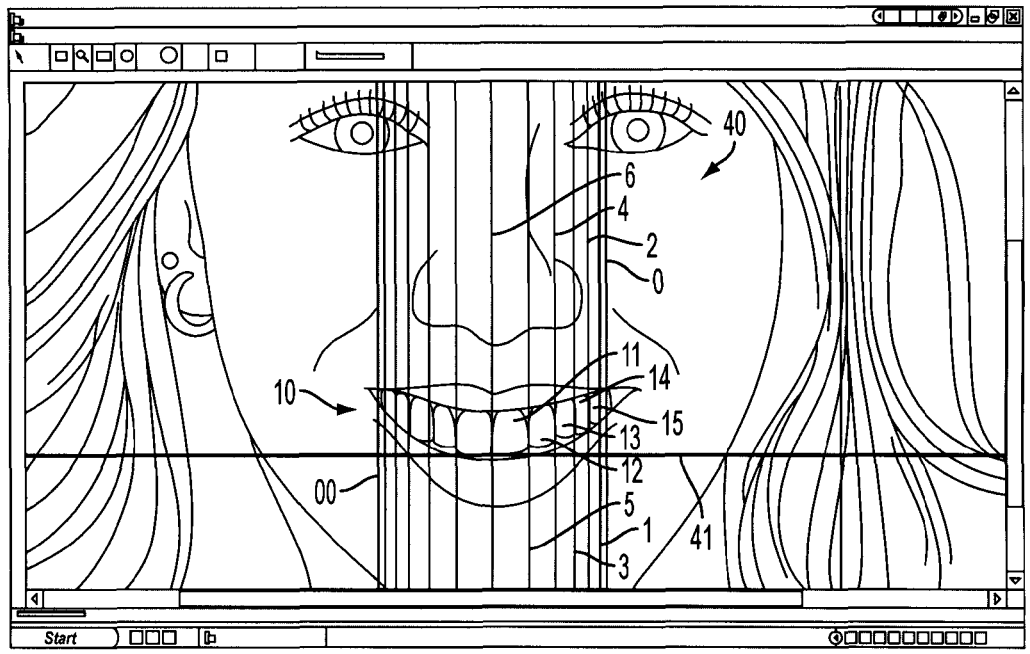
FIG. 21 is a front view image of the smile of an individual on which are superimposed Y axis and X axis positioning lines.

Referring to FIG. 21, the M Proportion with the positioning lines (6, 5, 4, 3, 2, 1, 0) in conjunction with the horizontal line (41) passing at the incisal edges of the centrals (11) is used in order to implement a digital facebow from a 2D facial photograph or a 3D facial photograph or 2D and 3D video to transfer the 3D position of the maxillary on an articulator or any 3D software.

The digital facebow replaces existing facebows or fox plates that are not accurate to wax up cases by using a simple facial photograph (40) of the patient in a frontal view. Accurate correlation between a 2D or 3D image or video and 3D model or cast is impossible using mechanical facebows. In the illustrative embodiment, the facial photograph (40) of the patient is taken while the patient looks to the horizon while having its head parallel to the floor so as to have the articulator parallel to the floor. The Frankfurt Plane can be used as a reference position to position the head of the patient parallel to the floor. Referring to FIG. 22, the Frankfurt Plane is a line (42) passing through two radiological points; the Porion (43) and the Orbitalis (44).

It is to be understood that a certain variance in the parallelism of the 2D photograph (40) or 3D photograph or video of the face of the patient to the floor is acceptable and does not compromise the transfer of the maxillary 3D position on the platform of the articulator or any 3D software for the functional or aesthetic side.

It is to be understood the digital facebow will position the model or cast of the teeth on the articulator in correlation with the teeth position on the image. For example the pre-op teeth on the image (40) will serve to mount the pre-op model or cast on the articulator. The provisional teeth on the image will serve to mount the provisional teeth on the model or cast. If the post-op model is mounted on the articulator: the post op teeth on the image will serve to mount the post op model or cast.

Each patient facial photograph (40) and each positioning of the vertical (110) and horizontal (111) lines on the facial photograph (40) will give different position of the model on the articulator and are treated as different digital facebow positions.

Facebows are used to transfer the maxillary position on an articulator with the upper maxillary centrals at an approximated distance of 110. mm from the hinge axis of the articulator, to mimic the anatomy of the masticatory system.

Figure 23:
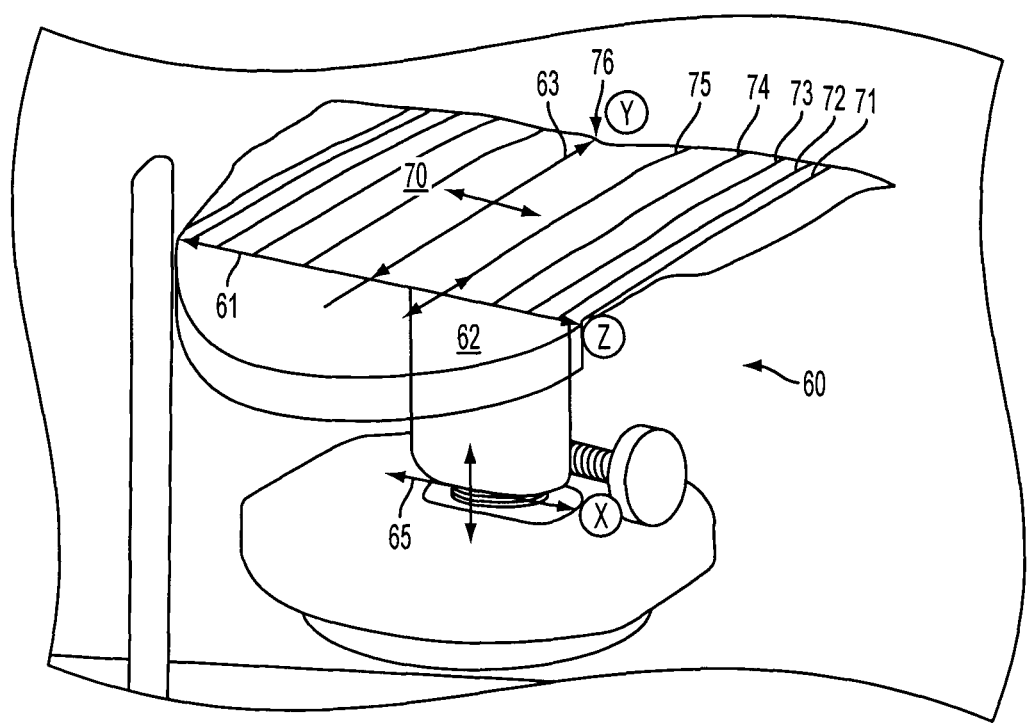
FIG. 23 is a top view of a platform on an articulator on which is applied the M Proportion ruler template.
Figure 48:
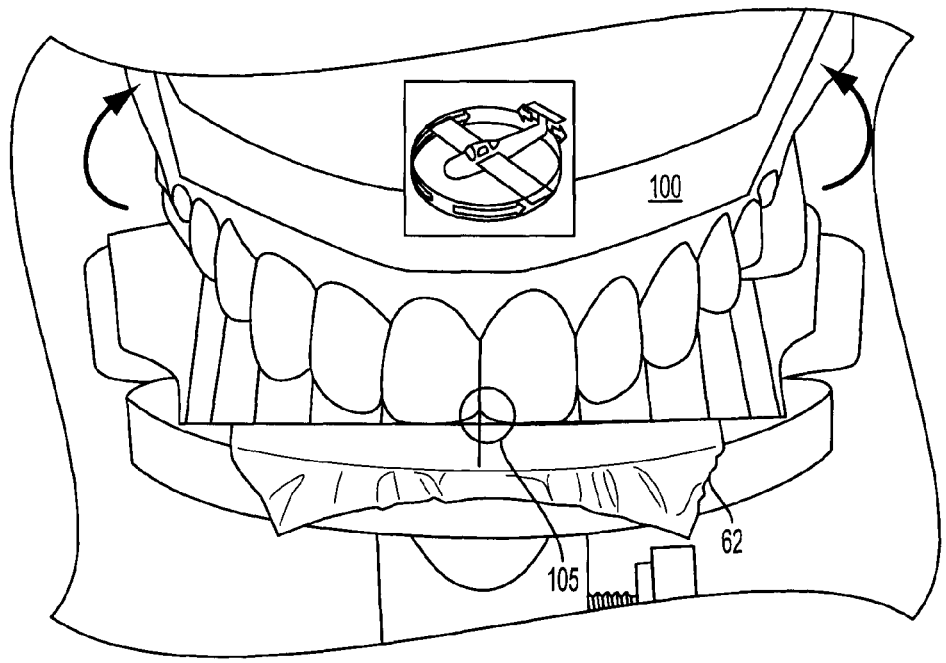
FIGS. 48 and 49 are illustrations of the alignment of the wax-up on a M Proportion ruler using three landmarks.
Figure 49:
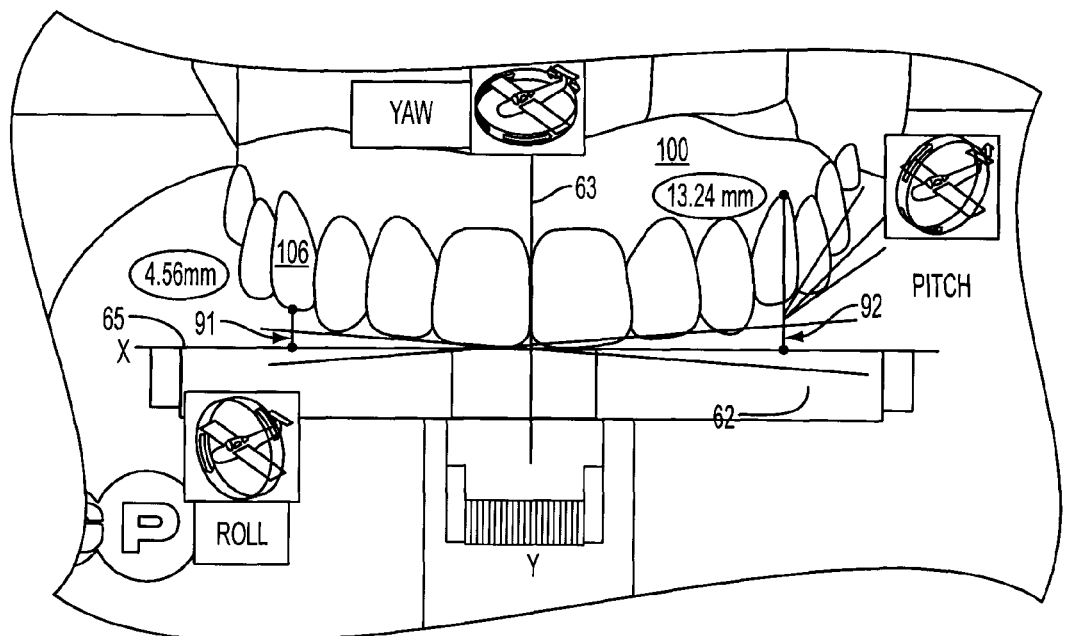

Referring to FIG. 23, it is possible to transfer, the position of the maxillary model or cast in 3D aero special position on an articulator (60) using the digital facebow, with a distance of 110 mm from the centrals to the hinge axis of the articulator by transferring the teeth positions in the X, Y and Z axis of the existing model on the installed platform (62) on the articulator (60). Referring to FIGS. 48 and 49, the X axis is positioning the Pitch and Roll and the Y axis is positioning the Yaw of the model or cast on the platform of the articulator.

Platforms exist in many manufacturing companies. The Z axis (61) is given by the teeth on the maxillary model or cast of the patient. The platform (62) on the articulator (60) has two lines, Z axis (61) and Y axis (63), crossing each other at approximately 110. mm from the hinge axis; depending of the brand of articulator (60) and platform (82). The adjustable and/or the M Proportion ruler is apposed against the Z axis line on the platform (62). The X and Y axis coordinates of the 2D pre op virtual wax up on the picture will be transpose in 3D on the pre-op model.

The Y axis

The adjustable and/or the M Proportion ruler provide the Y axis of the ideal position for each tooth in the maxillary. Referring to FIG. 26, a printed template (70) is positioned on the platform (62) against the Z axis line (61). The template (70) lines (71, 72, 73, 74, 75, 76) are positioned parallel to the center Y axis line (63) on the platform (62).

Figure 24:
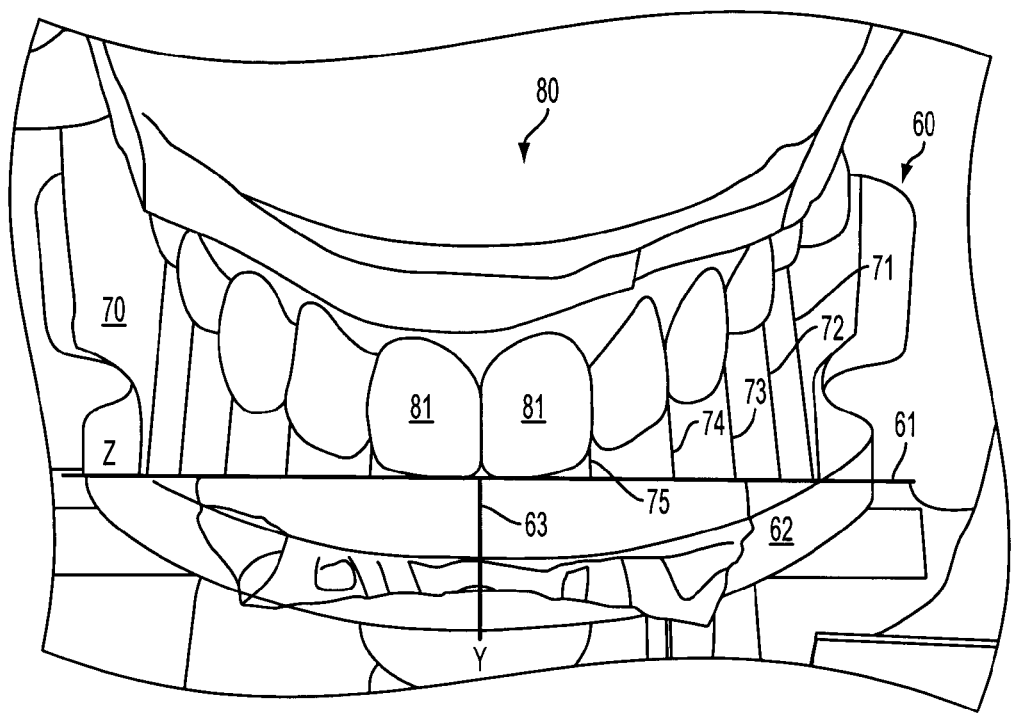
FIG. 24 shows the platform with a template on which is placed a maxillary model or cast.

Referring to FIG. 24, the maxillary model or cast (80) is then positioned on the template (70); the buccal edges of the centrals (81) of the maxillary model (80) are applied on the platform (70) against the Z axis line (61) and the midline of the centrals (81) is positioned on the midline of the template (70). In some cases were the dental midline needs to be moved on one side in the patient's mouth, the dental midline of the model or cast will not be positioned on the midline of the template. The midline of the model will be positioned on the original vertical centered line of the digital facebow passing through the midline of the pre-op centrals on the facial photograph.

Figure 25:
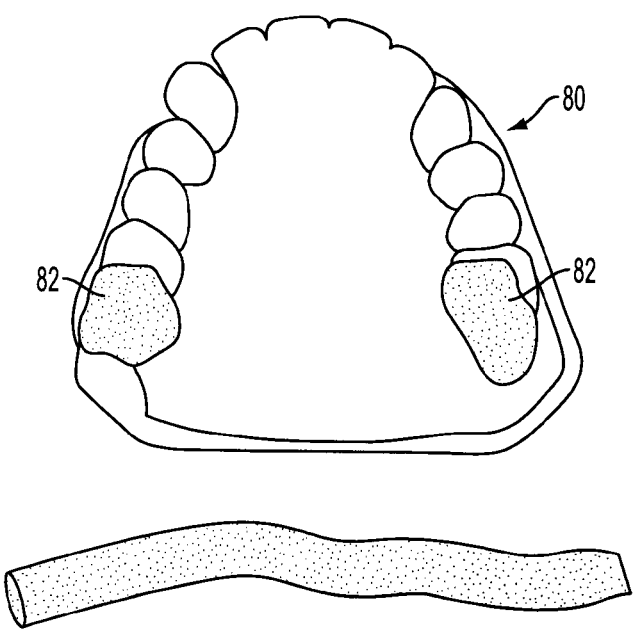
FIG. 25 is a bottom plan view of a maxillary model or cast on which pieces of wax or other adhesive are placed in the molar regions on each side.
Figure 26A:
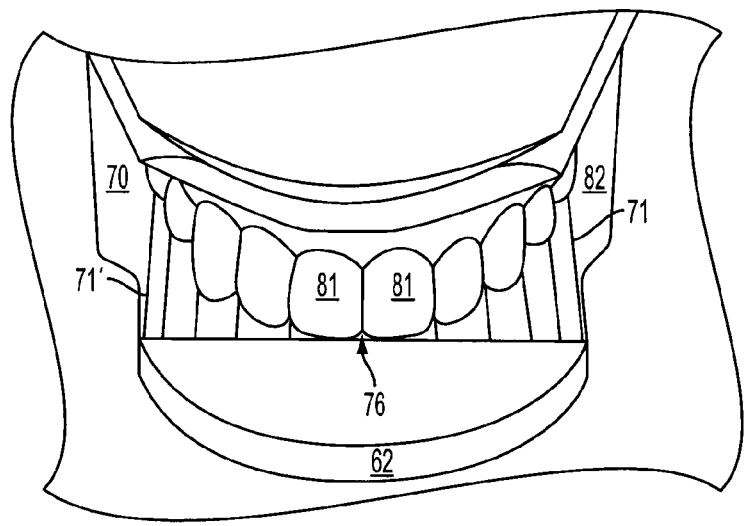
FIGS. 26A, 26B and 26C show a platform with a template on which is placed a maxillary model or cast with the pieces of wax or other adhesive.
Figure 26B:
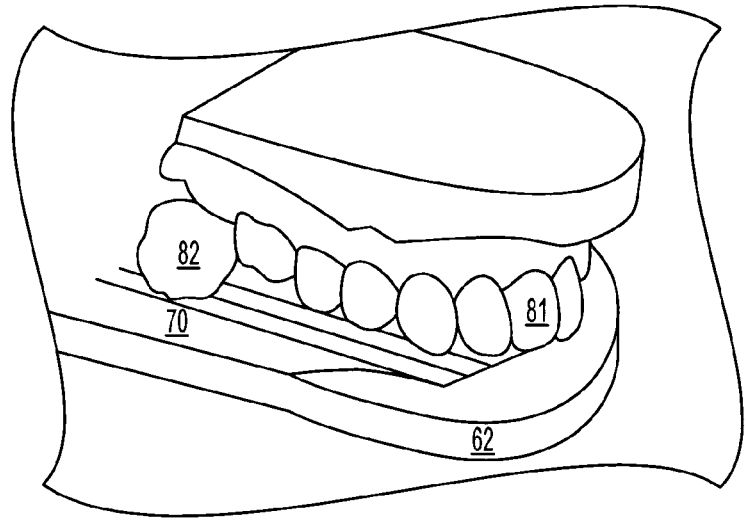
Figure 26C:
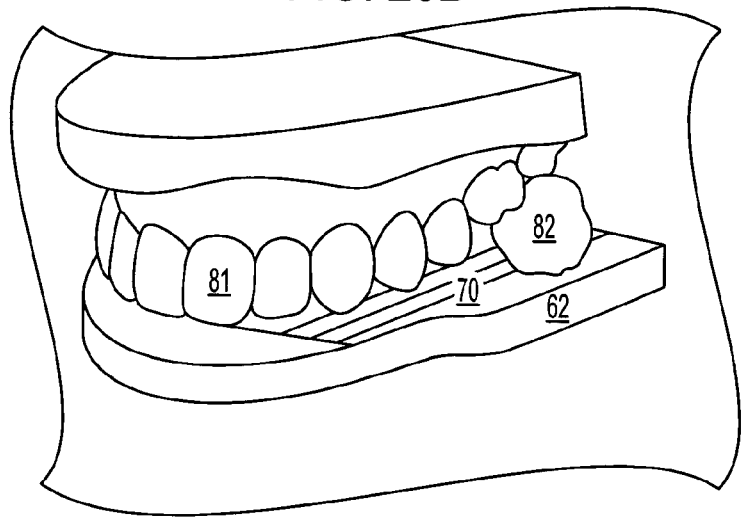

Referring now to FIG. 25, two pieces of wax (82) (or other adhesive or supporting material) are placed in the molar regions on each side and then, referring to FIGS. 26A, 26B and 26C, the model (80) is positioned on the template (70) relatively to the midline (76) and one of the last side lines on the left (71', 72') and right (71, 72) in correlation with the lines on the image showing the same teeth to secure de Yaw position. To achieve the correlation in the Yaw position between the image and the 3D model, the midline of the central on the model must be locked with the central line on the template of the platform (or locked on the original dental midline on the pre-op facial photograph if the midline is changed). The model is turned slightly on the left and/or the right to correlate the landmark position on each side of the model and the image.

It is to be understood that the digital facebow can be done with or without the template or M Proportions, as long as it meet the following requirements:

1—The image needs to be calibrated with the real measurements of the patient.
2—Combine with the rotation application using the intersection of the vertical and horizontal line at the junction of the dental midline and incisal edge of the upper centrals on an image with placement the same intersection of the vertical and horizontal line at the junction of the dental midline and incisal edge of the upper centrals of the correspondent model or cast of the teeth (shown on the image) on the platform of the articulator. For example any landmark on the model, at least one landmark on the right and one landmark on the left are needed to correlate with the image as long as it can be measured from the center line to the landmark on a side tooth (in the premolar or molar area) or the gum junction on the image and correlate those measurements from the center line to the landmark on the same side tooth or the gum junction on the platform. It is to be understood that each rotated image used to mount the model on the articulator as a specific position. With the same image, the model or cast can be mounted in as many positions as the intersection of the vertical and horizontal lines is applied on different position of the incisal edges and dental midline on the image. Those different positions of the model on the platform of the articulator and are treated as different digital facebow positions.

The X axis

Figure 27:
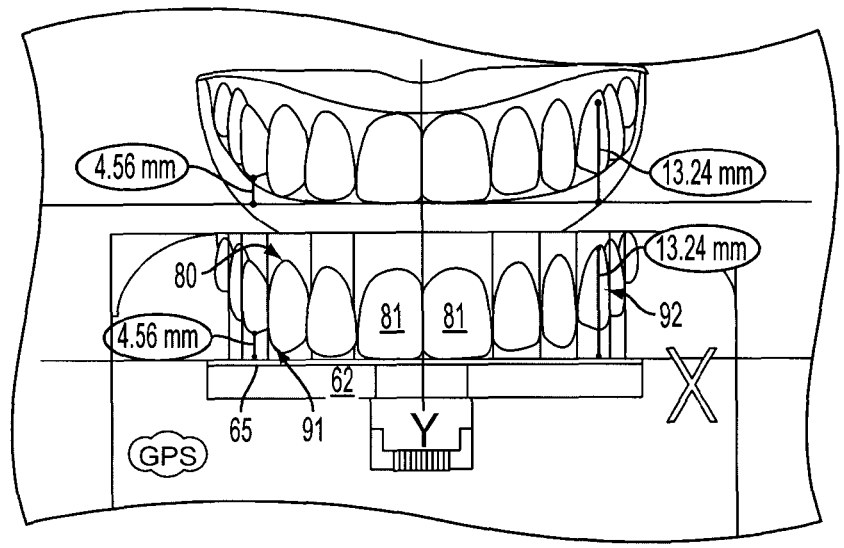
FIG. 27 is an elevation view of the platform with a template on which is aligned a maxillary model or cast.

Referring to FIG. 27, the 0 starting point on the X axis (65) is the top of the platform (62) from a frontal view. The X axis will determine the pitch and the roll of the model in 3D aero special position on the platform in correlation with the same measurements on the chosen teeth on the image.

Figure 28:
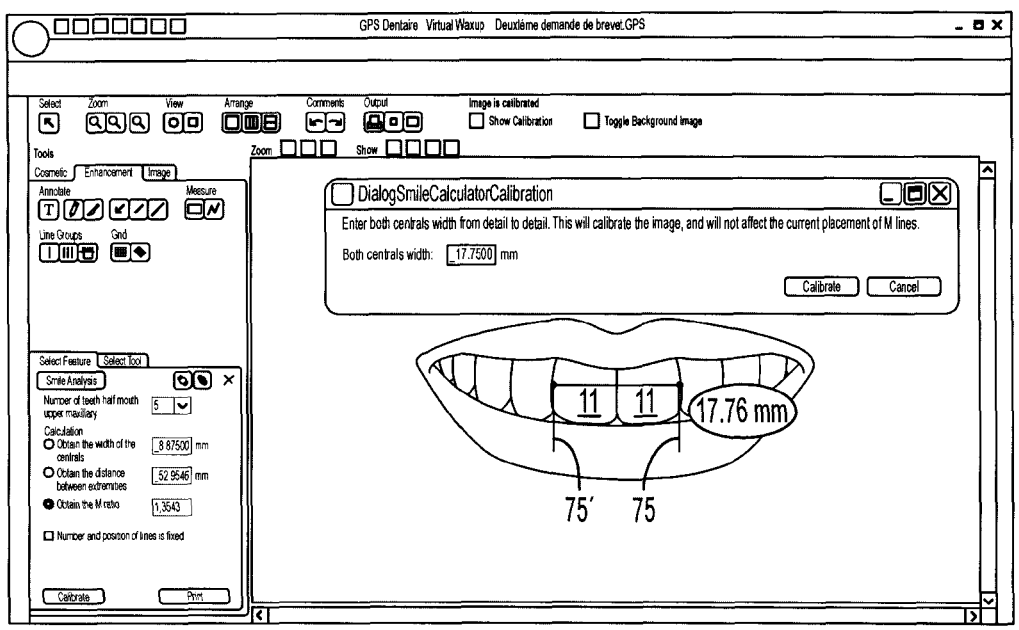
FIG. 28 is a front view image of the smile of an individual on which are superimposed the positioning lines and horizontal line of the M Proportion ruler and showing the calibration of the image.

Referring now to FIG. 28, both central widths from distal to distal is calibrated according to the first red lines of the M Proportion lines at the distal of the centrals (75, 75'). In the present example, both centrals (11) width is 17.75 mm, the M Proportion ruler central width is automatically calibrated at 8.8750. mm. The central width can be recalibrated at any time to insure an exact calibration of the measuring tool. The measuring tool is used to take the measurements of X and Y axis on the screen on the 2D photograph.

Figure 29:
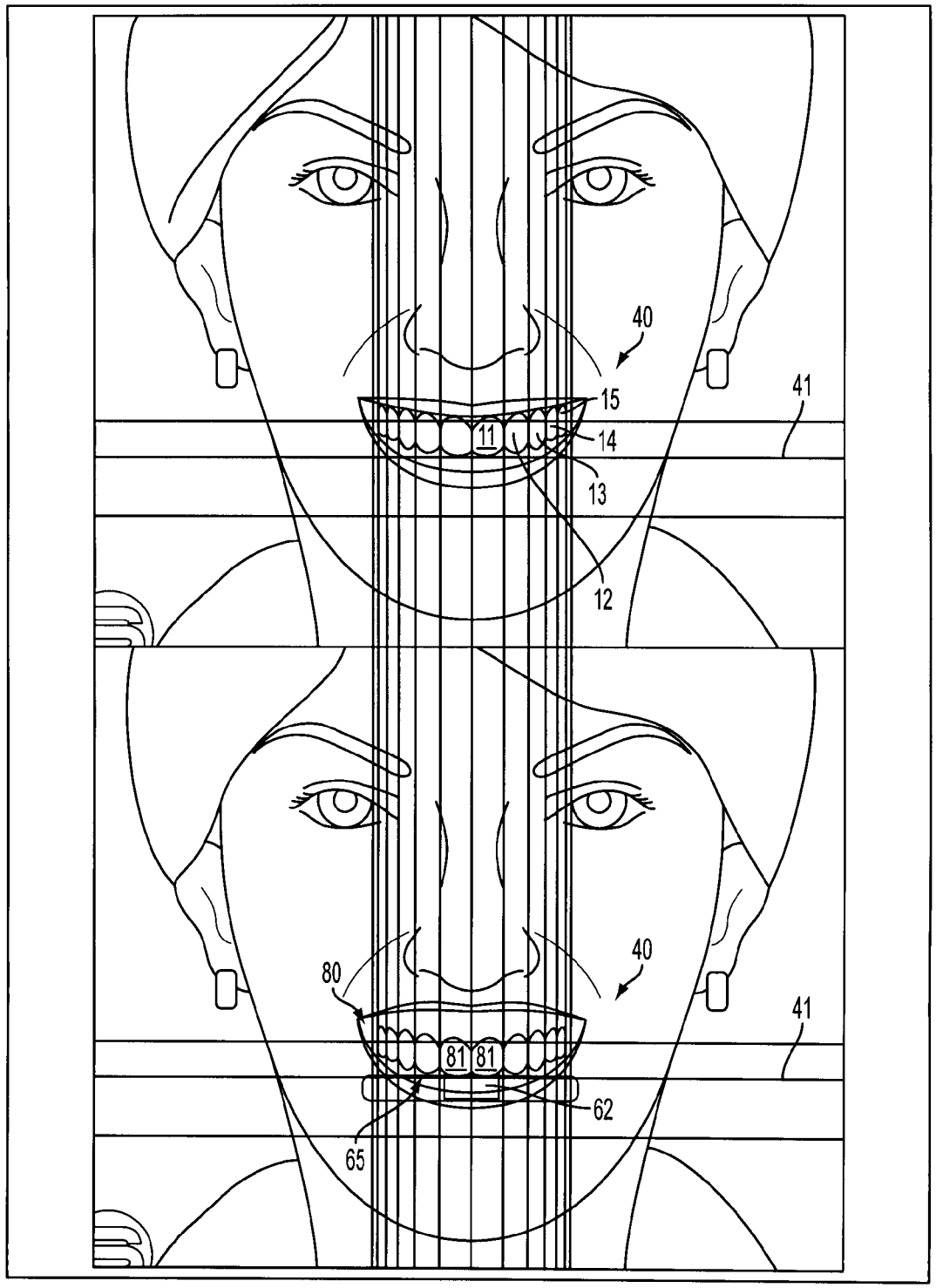
FIGS. 29 and 30 are front view images of the smile of an Individual on which are superimposed the positioning lines and horizontal line of the M Proportion ruler, and the platform with a template on which is aligned a maxillary model or cast.
Figure 30:
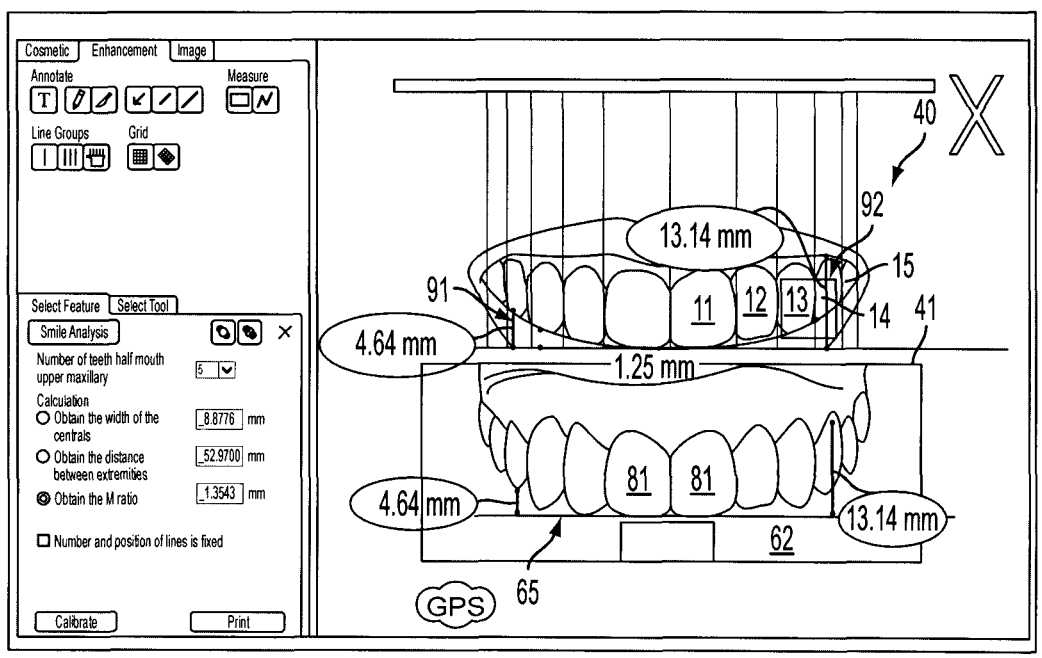
Figure 31:
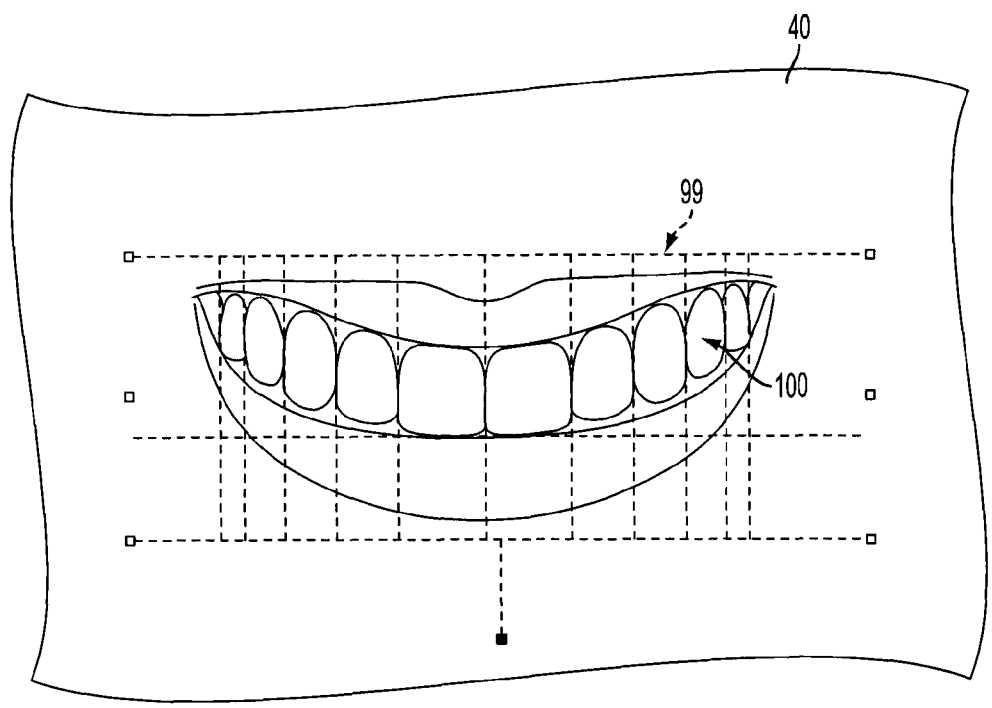
FIGS. 31 to 36 are front view images of the smile of an individual on which are superimposed M Proportion ruler and/or adjustable M Proportion ruler positioning lines attached to a smile library over the patient's teeth to achieve a virtual wax-up.

Referring to FIGS. 29 and 30, the incorporation of a horizontal line (41) to the M Proportion ruler passing at the incisal edges of the centrals (11) on the facial photograph (40) provides the X axis (65) representing the 0 starting point of the model (80) centrals (81), which is equal to the top of the platform (62) (see FIG. 27). Two measurements from the horizontal line (41) to the incisal (91) or gingival (92) edges are taken on the facial photograph (40); one on the left and the other on the right in the premolar or molar regions (14, 15) (best seen in FIG. 30).

It is to be understood that any reference point on any part of a tooth or gum junction on each side of the maxillary can be taken to correlate the image and the model on the platform.

Referring back to FIG. 27, those two measurements (91, 92) are used on the platform (62) representing the 0 starting point to position the maxillary model (80) with the right pitch and roll.

Transferring the 2D Virtual Wax Up to 3D Wax Up Manually

Figure 36:
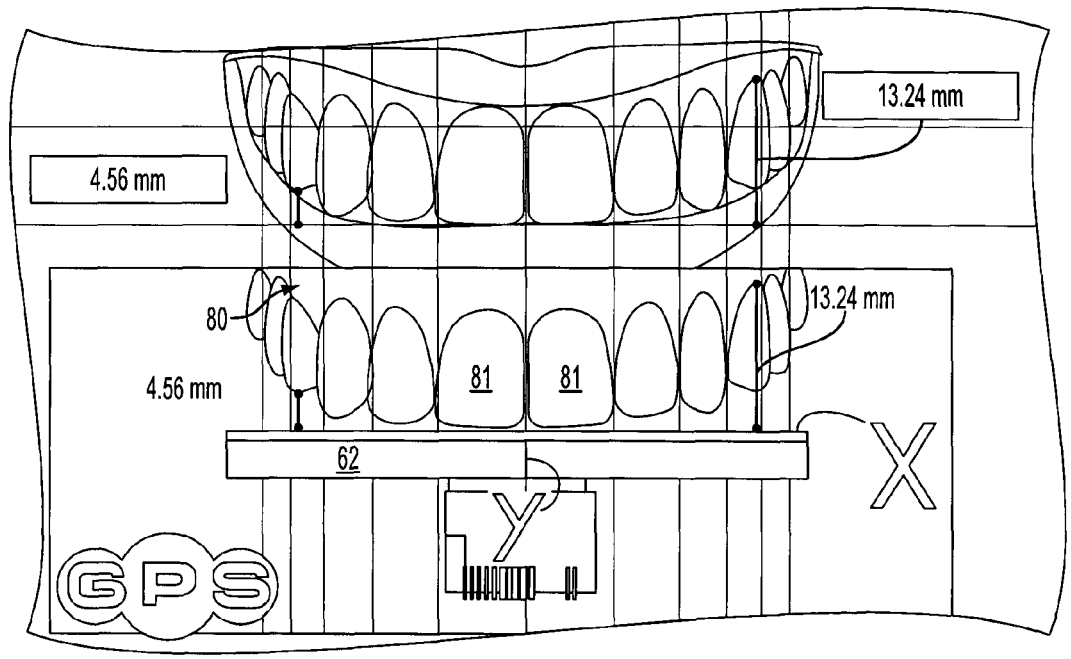

Referring to FIG. 36, both adjustable and/or M Proportion rulers can be printed on a template (70') and apposed on the platform (62) the virtual diagnostic wax-up for veneers, bridges and crowns will be achieved with the adjustable M Proportion, the best position for orthodontic treatment and dentures will be done with the M Proportion, i.e. model (80).

Figure 37:
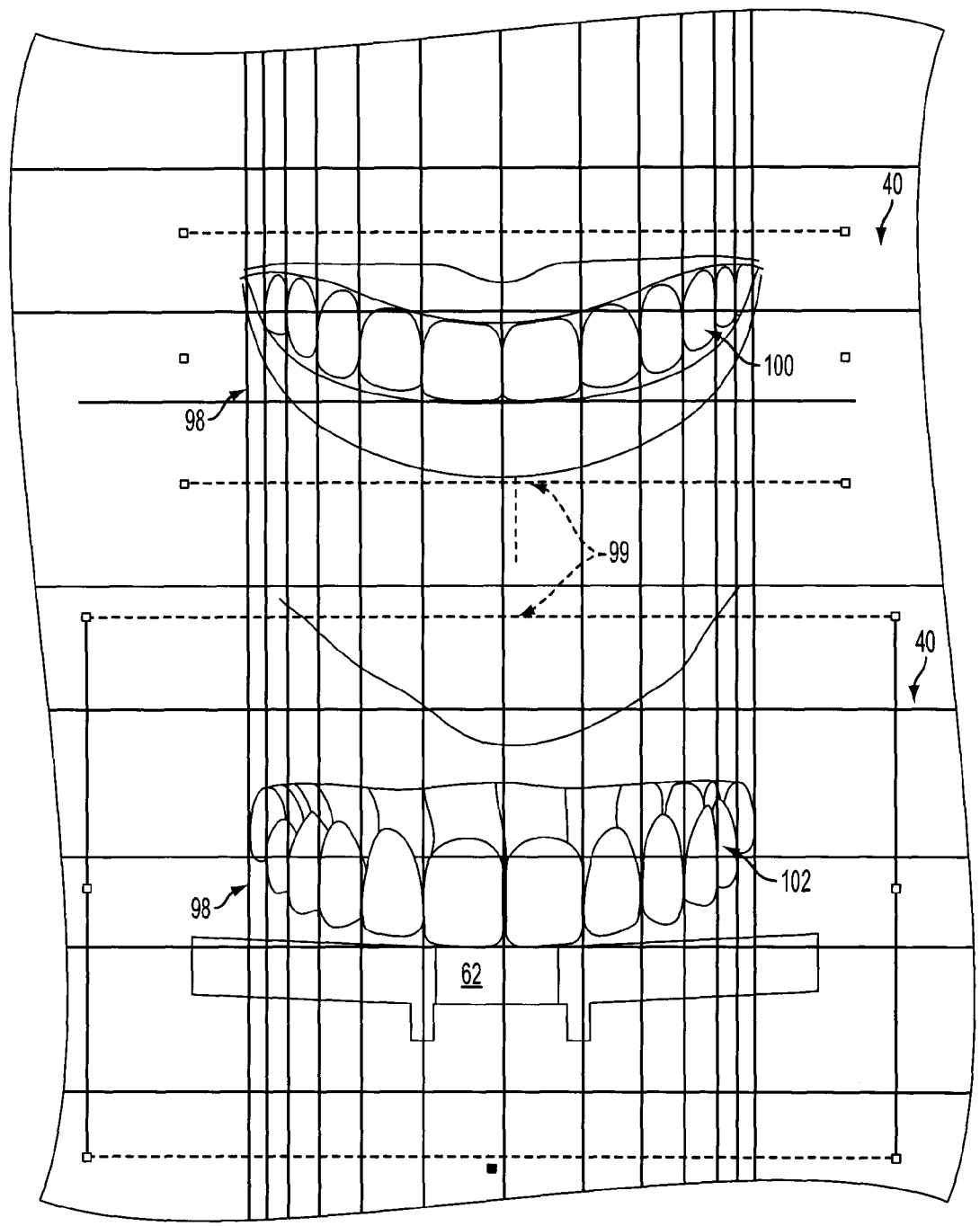
FIG. 37 is a front view image of the virtual diagnostic wax-up (new smile) of an individual on which are superimposed positioning lines of the adjustable M Proportion ruler bringing soft tissues and lips of the patient on the articulator by working in correlation with the position of the maxilla on the 2D image and the maxillary 3D model position or cast given by the digital facebow.
Figure 50:
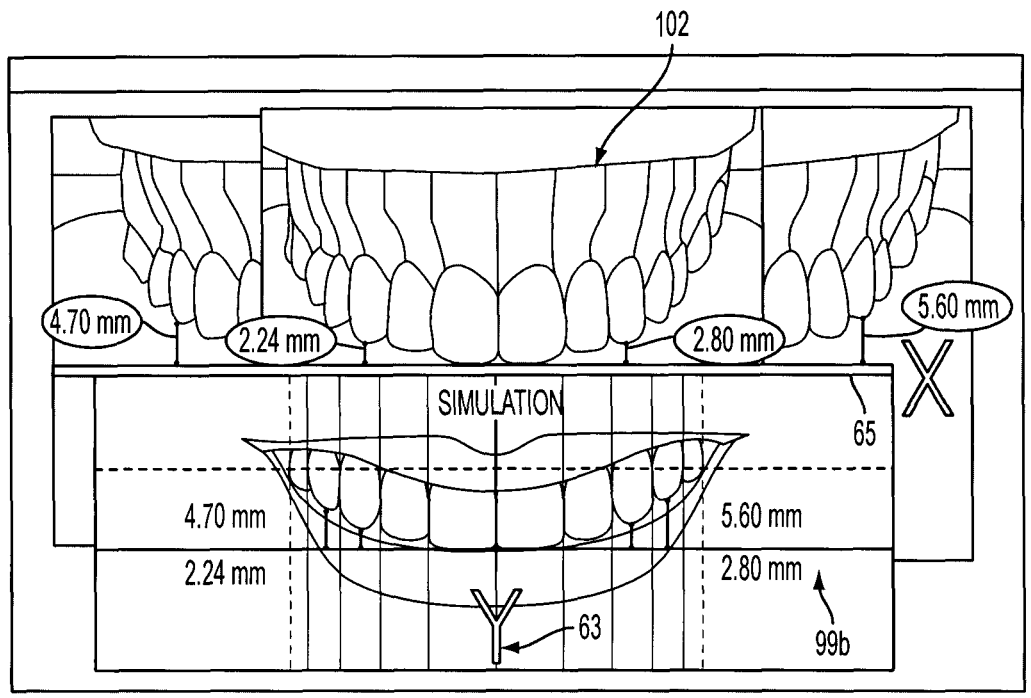
FIG. 50 is an illustration of the correlation between a 2D simulation and the final restoration.

Referring now to FIG. 37, both M (98) and adjustable M (99) Proportion rulers bring soft tissues and lips of the patient on the articulator by working in correlation with the position of the maxilla from the 2D image and the maxillary 3D model position on the articulator given by the digital facebow. The digital facebow function with both M and adjustable M Proportion rulers. The diagnostic wax-up (100) is done on the picture (40) with the adjustable M Proportion ruler respecting the smile line, the position of the lips, gingival architecture, axial inclinations, and emergence profile of each teeth, ect. The resulting virtual wax-up (100) is then transferred with the X and Y axis on the mounted model or cast to do the wax-up, i.e. (80) or the final restoration (102) manually by a dental technician or transferred to 3D software that will print or mill a cast of the 2D virtual wax-up. The 3D wax-up done manually or printed or milled or saved as a 3D file by 3D software will be used as the architectural plan to produce the final restorations. When the wax up is done manually by a lab technician, he will take the measurement in height from the X axis on the screen (the line passing through the incisal edge of the upper centrals) to the tip of each tooth in the virtual wax up in the image on the screen. The technician will also localize the position of the tip of the cusp between the medial and distal lines to localize the tip of each cusp on the wax up (102) (see FIG. 50). The lab technician will also mimic the morphology of the virtual wax up on the image to the wax up or the final restorations on the model or the cast.

Once the maxillary pre-op model is transferred on the articulator (60), the platform (62) is taken out of the articulator (60) to permit the mounting of the lower model in occlusion with the maxillary pre-op, wax-up, or final restorations model to verify the functional side of the wax up.

2D denture virtual set up and manual positioning of teeth

To match the pre-op facial photograph of the patient, the actual upper denture is duplicated in wax and is mounted on the platform of the articulator with the same technique describe for a patient with natural teeth. Before mounting the duplicated denture an accurate impression of the edentulous maxillary tissues have been taken with the duplication process or after and is mounted with the duplicated denture on the platform of the articulator. The same process can be done on the lower denture when both dentures are done at the same time by articulating the lower duplicated denture in occlusion with the upper duplicated denture.

In this method the denture pictures are in the 2D libraries. A variety of different dentures teeth in shape, size, and colors are stored in the 2D libraries from different suppliers. The correspondent 3D dentures have been scanned and placed in the 3D software. The denture libraries in the 2D software are calibrated with the central width and height of each for each set of dentures teeth. Those measurements are locked in the denture image with tracking lines that will stick to the adjustable or M Proportion lines on the teeth of the facial photograph.

The M Proportion ruler is placed and calibrated on the teeth of the patient actual denture or the trial denture over the patient facial photograph.

For each denture in the denture libraries placed in the patient mouth, the green lines in the picture of the library are fused to the red lines of the M Proportion on the patient's 2D photograph. The denture is adjusted automatically to the real size of the patient's mouth for the patient to visualize a realistic view of is future smile. The denture teeth are adapted to the lip and mouth of the patient with the movement of the adjustable M Proportion. The blue vertical lines are restricted to some minor adjustment of 0.5 mm on each side of the M Proportion (Red line) to make minor rotations. The upper horizontal line for the adjustment of the lip line (level of the upper gum), the middle horizontal line for the position of the incisal edges of the upper centrals, the length of the centrals is locked to, the size of the denture teeth insert over the patient's actual denture. The parabolic curvature blue box attached to the lower horizontal line adapts the occlusal plane to the smile line by draging the blue square up or down.

From the choosen denture library on the screen, the new set of teeth of that library are placed directly on the upper duplicated denture in wax. The technician will used the same technic as previously. All the teeth will be positionned in the wax of the upper duplicated denture with the template (of adjustable M Proportion or M Proportion ruler used for the set up on the screen.) on the platform of the articulator. This technic saves multiple appointments for the practionner and the patient.

Transferring the 2D Virtual Wax Up to a 3D Software Manufacturing a Computerized Wax Up Using 3D Modeling The 2D libraries are in the 2D software for consultation, diagnosis and treatment planning with the patient. The 3D correspondent libraries of the 2D images are in the 3D software. In this method the 2D virtual wax up placed over the patient pre op teeth in the 2D software is reproduced on the 3D pre op model of the patient inside the 3D software by overlaying the correspondent 3D library of the 2D library used in the 2D virtual wax up.

In the present method the 2D libraries used for virtual wax up come from real patient's mouth with natural teeth or restored teeth or it can come from other sources. All the smile and teeth pictures in the 2D libraries have their correspondent 3D model or cast stored and scanned In 3D The 2D smile project file interfaces is proceeding by automatic mesh alteration and the used same algorithm ratio, central width and inter molar width used in the 2D software. Once the 3D virtual wax up is overlaying the 3D pre-op model in the teeth data the lab technician will manually do alteration and adjustments on the teeth data model.

In the 3D software the wax up are done:
1—For dentures; 3D modeling of the smile under constraint (red lines). In this solution, the 3D model can admit small adjustments for each teeth
2—For crowns, veneers, bridges: 3D modeling of the smile that can be modified (blue lines). In this solution, the 3D model will adjust itself to the smile as a whole. The 3D model will have to respect the data from the patient (i.e. 2D coordinated (X, Y). anatomic reference points of the smile) as well as measurements from the wax model or scan of the mouth of the patient (i.e. depth in the Z axis).

Figure 51:
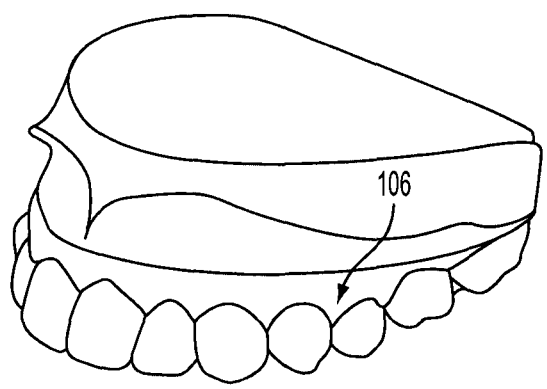
FIG. 51 shows a 3D model guide.
Figure 52:
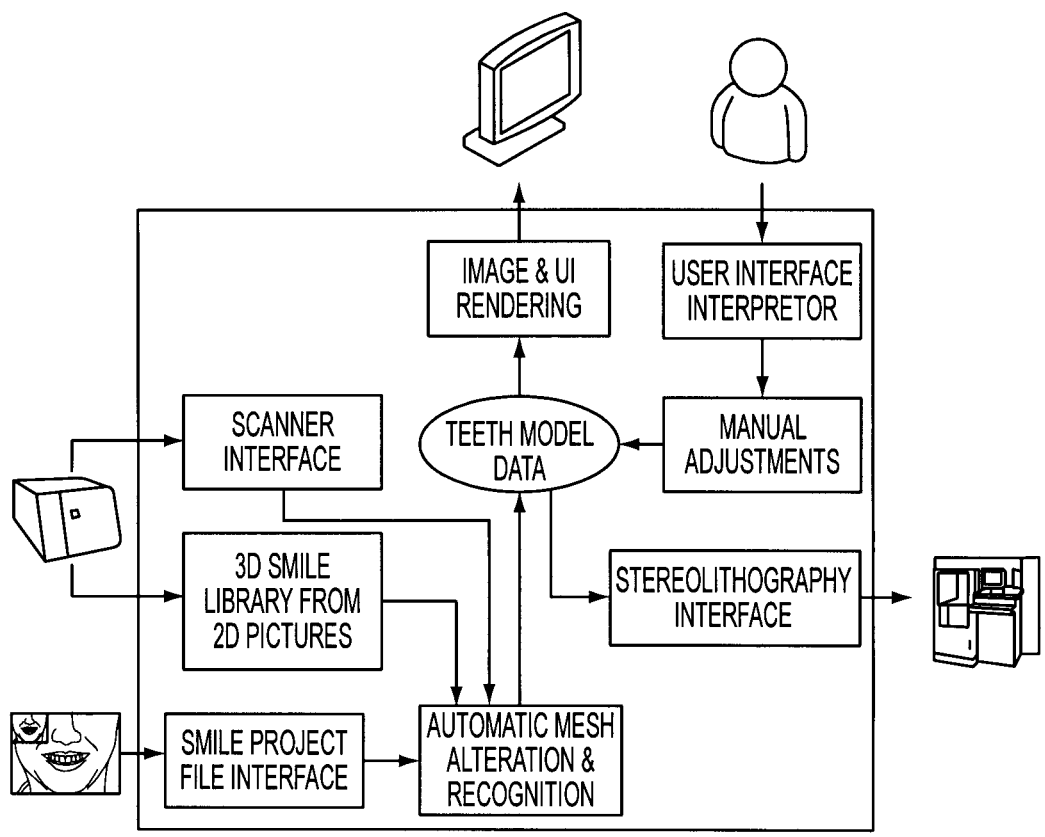
FIG. 52 is a block diagram of the dental analysis system.

Referring to this FIG. 51 a model of the 3D wax-up in the 3D software is printed by a stereolithographic printer. From that model a clear thin plastic shell (106) is done to guide the practitioner for the depth of cut for the placement of ceramic or other material as final restorations on the prepped teeth. A second clear plastic shell is done to produce the provisional's in the patient's mouth with a temporary composite material after prepping the teeth or putting abutment on implants to duplicate the virtual wax up in the patient's mouth.

Although the present disclosure has been described by way of an illustrative embodiment and example thereof, it should be noted that it will be apparent to persons skilled in the art that modifications may be applied to the present particular embodiment without departing from the scope of the present disclosure.

It is to be understood that the disclosed non-limitative illustrative embodiments may be used for assisting in various dental works such as, for example, surgery, fabrication and positioning of Implants, fabrication of ceramic veneers and crowns, fabrication of dentures, orthodontic molds, partial and complete prostheses, etc.

What is claimed is:

1. A system for designing the dentition of a patient, comprising:
an input for providing an image of the patient's smile to the system;
a memory having stored therein a library of digital images of smiles and of corresponding 3D dentition models wherein, in the library, each digital image of a smile is associated to a corresponding 3D dentition model;
a user interface for selecting a digital image of a smile to be applied to the image of the smile of the patient; and
a processor for:
applying a set of positioning indicators over the image of the patient's smile, the positioning indicators providing adjusted teeth positioning over the image of the patient's smile,
modifying, based on the positioning indicators, a 3D dentition model associated with the selected digital image of a smile, and
providing a virtual wax-up of a dental restoration of the dentition of the patient based on the modified 3D dentition model.

2. A system according to claim 1, wherein the user interface is configured so as to allow the adjustment of at least one of a pitch, yaw and roll of the associated 3D model.

3. A system according to claim 1, further comprising a scanner for acquiring at least one of a digital image of a smile and a 3D dentition model.

4. A system according to claim 3, further comprising a system to manufacture a 3D model guide of the virtual wax-up.

5. A system according to claim 3, further comprising a printer for providing a 3D model guide of the virtual wax-up.

6. A system according to claim 5, wherein the printer is a stereolitographic printer.

7. A system according to claim 1, wherein the processor processes a horizontal line passing at incisal edges of central incisors of the patient, at least one vertical line on the dental midline of the patient, and one vertical line passing on each side of the maxillary to implement a digital facebow from one of a 2D facial photograph, a 3D facial photograph, a 2D video, or a 3D video.

8. A system according to claim 7, wherein the processor uses the digital facebow to transfer a 3D position of the maxillary on an articulator or a 3D software.

9. A system according to claim 1, wherein the library of digital images of smiles comprises a library of 2D digital images of smiles.

10. A system according to claim 1, wherein the processor is further configured to:
define a first axis passing substantially at incisal edges of central incisors of the image of the patient's smile;
define a second axis substantially on the dental midline of the image of the patient's smile, the second axis being substantially perpendicular to the first axis; and
define coordinates of the virtual wax-up based on the first and second axes.

11. The system according to claim 10, wherein the coordinates of the virtual wax-up and the first and second axes of the image of the patient's smile are transferable on an articulator, allowing to adjust, on the articulator, a pitch and a roll of a pre op model of the patient about the first axis and to adjust a yaw of the pre op model of the patient about the second axis.

12. The system according to claim 10, wherein adjustments of the pitch, yaw and roll of the pre op model of the patient allow to produce a real wax-up based on the coordinates of the virtual wax-up and on an adjusted position of the pre op model.

13. The system according to claim 10, wherein the coordinates of the virtual wax-up and the first and second axes of the image of the patient's smile are transferable in a 3D software, allowing to adjust, in the 3D software, a pitch, a roll and a yaw of the 3D dentition model of the patient.

14. The system according to claim 13, wherein adjustments of the pitch, yaw and roll of the 3D dentition model of the patient allow to produce a real wax-up based on the coordinates of the virtual wax-up and on an adjusted position of the 3D dentition model of the patient.

15. A system according to claim 1, wherein the library is stored in the memory before the provision of the image of the patient's smile to the system.

16. A system according to claim 1, wherein the library contains information from one or more suppliers.

17. A system for positioning a 3D model of the maxillary of a patient on an articulator or 3D software, comprising:
an input for providing one of a 2D facial photograph, a 3D facial photograph, a 2D video, or a 3D video; and
a processor for implementing a digital facebow by placing, on the one of the 2D facial photograph, 3D facial photograph, 2D video, or 3D video, a horizontal line passing at incisal edges of central incisors of the patient to define a first axis, at least one vertical line on or near the dental midline of the patient to define a second axis, and one reference point on each side of the maxillary to define vertical distances between the first axis and the reference points, the processor defining the positioning of the 3D model based on the placement of the first axis and of the second axis, and based on the vertical distances between the first axis and the reference points.

18. A system according to claim 17, wherein the processor uses the digital facebow to transfer a 3D position of the maxillary on the articulator or on the 3D software.

19. A system according to claim 17, comprising a user interface configured so as to allow the adjustment of at least one of a pitch, yaw and roll on the 3D model of the maxillary of the patient.

* * * * *